US005424410A

United States Patent [19]

Payne et al.

[11] Patent Number: 5,424,410

[45] Date of Patent: Jun. 13, 1995

[54] *BACILLUS THURINGIENSIS* ISOLATES FOR CONTROLLING ACARIDES

[75] Inventors: Jewel M. Payne, San Diego, Calif.; Raymond J. C. Cannon; Angela L. Bagley, both of Kent, Great Britain

[73] Assignee: Mycogen Corporation, San Digeo, Calif.

[21] Appl. No.: 147,188

[22] Filed: Nov. 3, 1993

Related U.S. Application Data

[60] Division of Ser. No. 867,280, Apr. 30, 1992, Pat. No. 5,262,158, which is a continuation-in-part of Ser. No. 693,210, Apr. 30, 1991, abandoned, and Ser. No. 768,141, Sep. 30, 1991, Pat. No. 5,211,946, which is a continuation-in-part of Ser. No. 759,248, Sep. 13, 1991, abandoned.

[51] Int. Cl.[6] .................... A01N 63/00; A61K 37/00; C12N 15/00; C07H 19/00

[52] U.S. Cl. .................... 536/23.71; 424/93.4; 424/93.46; 424/93.461; 435/172.3; 435/242; 435/252.3; 435/252.5; 435/252.8; 435/320.1; 435/832; 536/22.1; 536/23.1; 536/23.2; 536/23.7

[58] Field of Search ................ 424/93 D, 93 L, 93 K; 435/172.3, 242, 252.3, 252.5, 252.8, 320.1, 832; 536/22.1, 23.1, 23.2, 23.7, 23.71

[56] References Cited

U.S. PATENT DOCUMENTS

| | | | |
|---|---|---|---|
| 4,695,455 | 9/1987 | Barnes et al. | 424/93 |
| 4,771,131 | 9/1988 | Herrnstadt et al. | 536/27 |
| 4,849,217 | 7/1989 | Soares et al. | 424/93 |

OTHER PUBLICATIONS

Couch, Terry L. (1980) "Mosquito Pathogenicity of *Bacillus thuringiensis* var. *israelensis*" *Developements in Industrial Microbiology 22:61–67.*

Beegle, Clayton C. (1978) "Use of Entomogenous Bacteria in Agroecosystems" Developments in Industrial Microbiology 20:97–104.

Royalty, Reen N. et al. (1990) "Effects of Thuriensin on *Tetranychus urticae*)acari: Tetranychidae) Mortality, Fecundity, and Feeding" J. Econ. Entomol. 83:792–798.

Neal, John W. et al. (1987) "Activity of the Thermostable Beta–Exotoxin of *Bacillus thuringiensis* Berliner on *Tetranychus urticae* and *T. Cinnabarinus*" J. Agric. Entomol. 4:33–40.

Vlayen, P. et al. (1978) "Activite D'une Preparation Commerciale de *Bacillus thuringiensis* sur L'Acarien Tisserand Commun *Tetranychus urticae* Koch. (Acari: Tetranychidae)" Mededelingen 43:471–479.

*Primary Examiner*—Robert A. Wax
*Assistant Examiner*—Hyosuk Kim
*Attorney, Agent, or Firm*—Saliwanchik & Saliwanchik

[57] ABSTRACT

Disclosed and claimed are *Bacillus thuringiensis* isolates designated B.t. PS50C, B.t. PS86A1, B.t. PS69D1, B.t. PS72L1, B.t. PS75J1, B.t. PS83E5, B.t. PS45B1, B.t.. PS24J, B.t. PS94R3, B.t. PS17, B.t. PS62B1 and B.t. PS74G1 which are active against acaride pests. Thus, these isolates, or mutants thereof, can be used to control such pests. Further, genes encoding novel δ-endotoxins can be removed from these isolates and transferred to other host microbes, or plants. Expression of the δ-endotoxins in microbe hosts results in the control of acaride pests, whereas transformed plants become resistant to acaride pests.

2 Claims, 2 Drawing Sheets

A. *B.t.* PS50C
B. *B.t.* PS86A1
C. *B.t.* PS69D1
D. *B.t.* PS72L1
E. *B.t.* PS75J1
F. *B.t.* PS83E5

A. *B.t.* PS24J
B. *B.t.* PS94R3
C. *B.t.* PS45B1

D. *B.t.* PS17
E. *B.t.* PS62B1
F. *B.t.* PS74C1

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
( A ) LENGTH: 4155 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17a ( v i i ) IMMEDIATE SOURCE:
( B ) CLONE: E. coli NM522(pMYC 1627) NRRL B-18651

( x i ) SEQUENCE DESCRIPTION: SEQ ID NO:1:

ATGGCAATTT TAAATGAATT ATATCCATCT GTACCTTATA ATGTATTGGC GTATACGCCA 60

CCCTCTTTTT TACCTGATGC GGGTACACAA GCTACACCTG CTGACTTAAC AGCTTATGAA 120

CAATTGTTGA AAAATTTAGA AAAAGGGATA AATGCTGGAA CTTATTCGAA AGCAATAGCT 180

GATGTACTTA AAGGTATTTT TATAGATGAT ACAATAAATT ATCAAACATA TGTAAATATT 240

GGTTTAAGTT TAATTACATT AGCTGTACCG GAAATTGGTA TTTTTACACC TTTCATCGGT 300

TTGTTTTTTG CTGCATTGAA TAAACATGAT GCTCCACCTC CTCCTAATGC AAAAGATATA 360

TTTGAGGCTA TGAAACCAGC GATTCAAGAG ATGATTGATA GAACTTTAAC TGCGGATGAG 420

CAAACATTTT TAAATGGGGA AATAAGTGGT TTACAAAATT TAGCAGCAAG ATACCAGTCT 480

ACAATGGATG ATATTCAAAG CCATGGAGGA TTTAATAAGG TAGATTCTGG ATTAATTAAA 540

AAGTTTACAG ATGAGGTACT ATCTTTAAAT AGTTTTTATA CAGATCGTTT ACCTGTATTT 600

ATTACAGATA ATACAGCGGA TCGAACTTTG TTAGGTCTTC CTTATTATGC TATACTTGCG 660

AGCATGCATC TTATGTTATT AAGAGATATC ATTACTAAGG GTCCGACATG GGATTCTAAA 720

ATTAATTTCA CACCAGATGC AATTGATTCC TTTAAAACCG ATATTAAAAA TAATATAAAG 780

-continued

CTTTACTCTA AAACTATTTA TGACGTATTT CAGAAGGGAC TTGCTTCATA CGGAACGCCT 840
TCTGATTTAG AGTCCTTTGC AAAAAAACAA AAATATATTG AAATTATGAC AACACATTGT 900
TTAGATTTTG CAAGATTGTT TCCTACTTTT GATCCAGATC TTTATCCAAC AGGATCAGGT 960
GATATAAGTT TACAAAAAAC ACGTAGAATT CTTTCTCCTT TTATCCCTAT ACGTACTGCA 1020
GATGGGTTAA CATTAAATAA TACTTCAATT GATACTTCAA ATTGGCCTAA TTATGAAAAT 1080
GGGAATGGCG CGTTTCCAAA CCCAAAAGAA AGAATATTAA AACAATTCAA ACTGTATCCT 1140
AGTTGGAGAG CGGGACAGTA CGGTGGGCTT TTACAACCTT ATTTATGGGC AATAGAAGTC 1200
CAAGATTCTG TAGAGACTCG TTTGTATGGG CAGCTTCCAG CTGTAGATCC ACAGGCAGGG 1260
CCTAATTATG TTTCCATAGA TTCTTCTAAT CCAATCATAC AAATAAATAT GGATACTTGG 1320
AAAACACCAC CACAAGGTGC GAGTGGGTGG AATACAAATT TAATGAGAGG AAGTGTAAGC 1380
GGGTTAAGTT TTTTACAACG AGATGGTACG AGACTTAGTG CTGGTATGGG TGGTGGTTTT 1440
GCTGATACAA TATATAGTCT CCCTGCAACT CATTATCTTT CTTATCTCTA TGGAACTCCT 1500
TATCAAACTT CTGATAACTA TTCTGGTCAC GTTGGTGCAT TGGTAGGTGT GAGTACGCCT 1560
CAAGAGGCTA CTCTTCCTAA TATTATAGGT CAACCAGATG AACAGGGAAA TGTATCTACA 1620
ATGGGATTTC CGTTTGAAAA AGCTTCTTAT GGAGGTACAG TTGTTAAAGA ATGGTTAAAT 1680
GGTGCGAATG CGATGAAGCT TTCTCCTGGG CAATCTATAG GTATTCCTAT TACAAATGTA 1740
ACAAGTGGAG AATATCAAAT TCGTTGTCGT TATGCAAGTA ATGATAATAC TAACGTTTTC 1800
TTTAATGTAG ATACTGGTGG AGCAAATCCA ATTTTCCAAC AGATAAACTT TGCATCTACT 1860
GTAGATAATA ATACGGGAGT ACAAGGAGCA AATGGTGTCT ATGTAGTCAA ATCTATTGCT 1920
ACAACTGATA ATTCTTTTAC AGAAATTCCT GCGAAGACGA TTAATGTTCA TTTAACCAAC 1980
CAAGGTTCTT CTGATGTCTT TTTAGACCGT ATTGAATTTA TACCTTTTTC TCTACCTCTT 2040
ATATATCATG GAAGTTATAA TACTTCATCA GGTGCAGATG ATGTTTTATG GTCTTCTTCA 2100
AATATGAATT ACTACGATAT AATAGTAAAT GGTCAGGCCA ATAGTAGTAG TATCGCTAGT 2160
TCTATGCATT TGCTTAATAA AGGAAAAGTG ATAAAAACAA TTGATATTCC AGGGCATTCG 2220
GAAACCTTCT TTGCTACGTT CCCAGTTCCA GAAGGATTTA ATGAAGTTAG AATTCTTGCT 2280
GGCCTTCCAG AAGTTAGTGG AAATATTACC GTACAATCTA ATAATCCGCC TCAACCTAGT 2340
AATAATGGTG GTGGTGATGG TGGTGGTAAT GGTGGTGGTG ATGGTGGTCA ATACAATTTT 2400
TCTTTAAGCG GATCTGATCA TACGACTATT TATCATGGAA AACTTGAAAC TGGGATTCAT 2460
GTACAAGGTA ATTATACCTA TACAGGTACT CCCGTATTAA TACTGAATGC TTACAGAAAT 2520
AATACTGTAG TATCAAGCAT TCCAGTATAT TCTCCTTTTG ATATAACTAT ACAGACAGAA 2580
GCTGATAGCC TTGAGCTTGA ACTACAACCT AGATATGGTT TTGCCACAGT GAATGGTACT 2640
GCAACAGTAA AAAGTCCTAA TGTAAATTAC GATAGATCAT TTAAACTCCC AATAGACTTA 2700
CAAAATATCA CAACACAAGT AAATGCATTA TTCGCATCTG GAACACAAAA TATGCTTGCT 2760
CATAATGTAA GTGATCATGA TATTGAAGAA GTTGTATTAA AAGTGGATGC CTTATCAGAT 2820
GAAGTATTTG GAGATGAGAA GAAGGCTTTA CGTAAATTGG TGAATCAAGC AAAACGTTTG 2880
AGTAGAGCAA GAAATCTTCT GATAGGTGGG AGTTTTGAAA ATTGGGATGC ATGGTATAHA 2940
GGAAGAAATG TAGTAACTGT ATCTGATCAT GAACTATTTA AGAGTGATCA TGTATTATTA 3000
CCACCACCAG GATTGTCTCC ATCTTATATT TTCCAAAAAG TGGAGGAATC TAAATTAAAA 3060
CCAAATACAC GTTATATTGT TTCTGGATTC ATCGCACATG GAAAAGACCT AGAAATTGTT 3120
GTTTCACGTT ATGGGCAAGA AGTGCAAAAG GTCGTGCAAG TTCCTTATGG AGAAGCATTC 3180
CCGTTAACAT CAAATGGACC AGTTTGTTGT CCCCCACGTT CTACAAGTAA TGGAACCTTA 3240

-continued

```
GGAGATCCAC ATTTCTTTAG TTACAGTATC GATGTAGGTG CACTAGATTT ACAAGCAAAC 3300
CCTGGTATTG AATTTGGTCT TCGTATTGTA AATCCAACTG GAATGGCACG CGTAAGCAAT 3360
TTGGAAATTC GTGAAGATCG TCCATTAGCA GCAAATGAAA TACGACAAGT ACAACGTGTC 3420
GCAAGAAATT GGAGAACCGA GTATGAGAAA GAACGTGCGG AAGTAACAAG TTTAATTCAA 3480
CCTGTTATCA ATCGAATCAA CGGATTGTAT GAAAATGGAA ATTGGAACGG TTCTATTCGT 3540
TCAGATATTT CGTATCAGAA TATAGACGCG ATTGTATTAC CAACGTTACC AAAGTTACGC 3600
CATTGGTTTA TGTCAGATAG ATTCAGTGAA CAAGGAGATA TAATGGCTAA ATTCCAAGGT 3660
GCATTAAATC GTGCGTATGC ACAACTGGAA CAAAGTACGC TTCTGCATAA TGGTCATTTT 3720
ACAAAAGATG CAGCTAATTG GACAATAGAA GGCGATGCAC ATCAGATAAC ACTAGAAGAT 3780
GGTAGACGTG TATTGCGACT TCCAGATTGG TCTTCGAGTG TATCTCAAAT GATTGA&ATC 3840
GAGAATTTTA ATCCAGATAA AGAATACAAC TTAGTATTCC ATGGGCAAGG AGAAGGAACG 3900
GTTACGTTGG AGCATGGAGA AGAAACAAAA TATATAGAAA CGCATACACA TCATTTTGCG 3960
AATTTTACAA CTTCTCAACG TCAAGGACTC ACGTTTGAAT CAAATAAAGT GACAGTGACC 4020
ATTTCTTCAG AAGATGGAGA ATTCTTAGTG GATAATATTG CGCTTGTGGA AGCTCCTCTT 4080
CCTACAGATG ACCAAAATTC TGAGGGAAAT ACGGCTTCCA GTACGAATAG CGATACAAGT 4140
ATGAACAACA ATCAA                                                  4155
```

( 2 ) INFORMATION FOR SEQ ID NO:2:

( i ) SEQUENCE CHARACTERISTICS:
( A ) LENGTH: 1385 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS17

( v i i ) IMMEDIATE SOURCE:
( B ) CLONE: E. coli NM522(pMYC 1627) NRRL B-18651

( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ala | Ile | Leu | Asn | Glu | Leu | Tyr | Pro | Ser | Val | Pro | Tyr | Asn | Val | Leu |
| 1 | | | | 5 | | | | | 10 | | | | | 15 | |
| Ala | Tyr | Thr | Pro | Pro | Ser | Phe | Leu | Pro | Asp | Ala | Gly | Thr | Gln | Ala | Thr |
| | | | 20 | | | | | 25 | | | | | 30 | | |
| Pro | Ala | Asp | Leu | Thr | Ala | Tyr | Glu | Gln | Leu | Leu | Lys | Asn | Leu | Glu | Lys |
| | | 35 | | | | | 40 | | | | | 45 | | | |
| Gly | Ile | Asn | Ala | Gly | Thr | Tyr | Ser | Lys | Ala | Ile | Ala | Asp | Val | Leu | Lys |
| | 50 | | | | | 55 | | | | | 60 | | | | |
| Gly | Ile | Phe | Ile | Asp | Asp | Thr | Ile | Asn | Tyr | Gln | Thr | Tyr | Val | Asn | Ile |
| 65 | | | | | 70 | | | | | 75 | | | | | 80 |
| Gly | Leu | Ser | Leu | Ile | Thr | Leu | Ala | Val | Pro | Glu | Ile | Gly | Ile | Phe | Thr |
| | | | | 85 | | | | | 90 | | | | | 95 | |
| Pro | Phe | Ile | Gly | Leu | Phe | Phe | Ala | Ala | Leu | Asn | Lys | His | Asp | Ala | Pro |
| | | | 100 | | | | | 105 | | | | | 110 | | |
| Pro | Pro | Pro | Asn | Ala | Lys | Asp | Ile | Phe | Glu | Ala | Met | Lys | Pro | Ala | Ile |
| | | 115 | | | | | 120 | | | | | 125 | | | |
| Gln | Glu | Met | Ile | Asp | Arg | Thr | Leu | Thr | Ala | Asp | Glu | Gln | Thr | Phe | Leu |
| | 130 | | | | | 135 | | | | | 140 | | | | |

-continued

Asn Gly Glu Ile Ser Gly Leu Gln Asn Leu Ala Ala Arg Tyr Gln Ser
145 150 155 160

Thr Met Asp Asp Ile Gln Ser His Gly Gly Phe Asn Lys Val Asp Ser
165 170 175

Gly Leu Ile Lys Lys Phe Thr Asp Glu Val Leu Ser Leu Asn Ser Phe
180 185 190

Tyr Thr Asp Arg Leu Pro Val Phe Ile Thr Asp Asn Thr Ala Asp Arg
195 200 205

Thr Leu Leu Gly Leu Pro Tyr Tyr Ala Ile Leu Ala Ser Met His Leu
210 215 220

Met Leu Leu Arg Asp Ile Ile Thr Lys Gly Pro Thr Trp Asp Ser Lys
225 230 235 240

Ile Asn Phe Thr Pro Asp Ala Ile Asp Ser Phe Lys Thr Asp Ile Lys
245 250 255

Asn Asn Ile Lys Leu Tyr Ser Lys Thr Ile Tyr Asp Val Phe Gln Lys
260 265 270

Gly Leu Ala Ser Tyr Gly Thr Pro Ser Asp Leu Glu Ser Phe Ala Lys
275 280 285

Lys Gln Lys Tyr Ile Glu Ile Met Thr Thr His Cys Leu Asp Phe Ala
290 295 300

Arg Leu Phe Pro Thr Phe Asp Pro Asp Leu Tyr Pro Thr Gly Ser Gly
305 310 315 320

Asp Ile Ser Leu Gln Lys Thr Arg Arg Ile Leu Ser Pro Phe Ile Pro
325 330 335

Ile Arg Thr Ala Asp Gly Leu Thr Leu Asn Asn Thr Ser Ile Asp Thr
340 345 350

Ser Asn Trp Pro Asn Tyr Glu Asn Gly Asn Gly Ala Phe Pro Asn Pro
355 360 365

Lys Glu Arg Ile Leu Lys Gln Phe Lys Leu Tyr Pro Ser Trp Arg Ala
370 375 380

Gly Gln Tyr Gly Gly Leu Leu Gln Pro Tyr Leu Trp Ala Ile Glu Val
385 390 395 400

Gln Asp Ser Val Glu Thr Arg Leu Tyr Gly Gln Leu Pro Ala Val Asp
405 410 415

Pro Gln Ala Gly Pro Asn Tyr Val Ser Ile Asp Ser Ser Asn Pro Ile
420 425 430

Ile Gln Ile Asn Met Asp Thr Trp Lys Thr Pro Pro Gln Gly Ala Ser
435 440 445

Gly Trp Asn Thr Asn Leu Met Arg Gly Ser Val Ser Gly Leu Ser Phe
450 455 460

Leu Gln Arg Asp Gly Thr Arg Leu Ser Ala Gly Met Gly Gly Gly Phe
465 470 475 480

Ala Asp Thr Ile Tyr Ser Leu Pro Ala Thr His Tyr Leu Ser Tyr Leu
485 490 495

Tyr Gly Thr Pro Tyr Gln Thr Ser Asp Asn Tyr Ser Gly His Val Gly
500 505 510

Ala Leu Val Gly Val Ser Thr Pro Gln Glu Ala Thr Leu Pro Asn Ile
515 520 525

Ile Gly Gln Pro Asp Glu Gln Gly Asn Val Ser Thr Met Gly Phe Pro
530 535 540

Phe Glu Lys Ala Ser Tyr Gly Gly Thr Val Val Lys Glu Trp Leu Asn
545 550 555 560

Gly Ala Asn Ala Met Lys Leu Ser Pro Gly Gln Ser Ile Gly Ile Pro
565 570 575

-continued

```
Ile Thr Asn Val Thr Ser Gly Glu Tyr Gln Ile Arg Cys Arg Tyr Ala
            580                 585                 590

Ser Asn Asp Asn Thr Asn Val Phe Phe Asn Val Asp Thr Gly Gly Ala
        595                 600                 605

Asn Pro Ile Phe Gln Gln Ile Asn Phe Ala Ser Thr Val Asp Asn Asn
    610                 615                 620

Thr Gly Val Gln Gly Ala Asn Gly Val Tyr Val Val Lys Ser Ile Ala
625                 630                 635                 640

Thr Thr Asp Asn Ser Phe Thr Glu Ile Pro Ala Lys Thr Ile Asn Val
                645                 650                 655

His Leu Thr Asn Gln Gly Ser Ser Asp Val Phe Leu Asp Arg Ile Glu
            660                 665                 670

Phe Ile Pro Phe Ser Leu Pro Leu Ile Tyr His Gly Ser Tyr Asn Thr
        675                 680                 685

Ser Ser Gly Ala Asp Asp Val Leu Trp Ser Ser Ser Asn Met Asn Tyr
    690                 695                 700

Tyr Asp Ile Ile Val Asn Gly Gln Ala Asn Ser Ser Ser Ile Ala Ser
705                 710                 715                 720

Ser Met His Leu Leu Asn Lys Gly Lys Val Ile Lys Thr Ile Asp Ile
                725                 730                 735

Pro Gly His Ser Glu Thr Phe Phe Ala Thr Phe Pro Val Pro Glu Gly
            740                 745                 750

Phe Asn Glu Val Arg Ile Leu Ala Gly Leu Pro Glu Val Ser Gly Agn
        755                 760                 765

Ile Thr Val Gln Ser Asn Asn Pro Pro Gln Pro Ser Asn Asn Gly Gly
    770                 775                 780

Gly Asp Gly Gly Gly Asn Gly Gly Gly Asp Gly Gly Gln Tyr Asn Phe
785                 790                 795                 800

Ser Leu Ser Gly Ser Asp His Thr Thr Ile Tyr His Gly Lys Leu Glu
                805                 810                 815

Thr Gly Ile His Val Gln Gly Asn Tyr Thr Tyr Thr Gly Thr Pro Val
            820                 825                 830

Leu Ile Leu Asn Ala Tyr Arg Asn Asn Thr Val Val Ser Ser Ile Pro
        835                 840                 845

Val Tyr Ser Pro Phe Asp Ile Thr Ile Gln Thr Glu Ala Asp Ser Leu
    850                 855                 860

Glu Leu Glu Leu Gln Pro Arg Tyr Gly Phe Ala Thr Val Asn Gly Thr
865                 870                 875                 880

Ala Thr Val Lys Ser Pro Asn Val Asn Tyr Asp Arg Ser Phe Lys Leu
                885                 890                 895

Pro Ile Asp Leu Gln Asn Ile Thr Thr Gln Val Asn Ala Leu Phe Ala
            900                 905                 910

Ser Gly Thr Gln Asn Met Leu Ala His Asn Val Ser Asp His Asp Ile
        915                 920                 925

Glu Glu Val Val Leu Lys Val Asp Ala Leu Ser Asp Glu Val Phe Gly
    930                 935                 940

Asp Glu Lys Lys Ala Leu Arg Lys Leu Val Asn Gln Ala Lys Arg Leu
945                 950                 955                 960

Ser Arg Ala Arg Asn Leu Leu Ile Gly Gly Ser Phe Glu Asn Trp Asp
                965                 970                 975

Ala Trp Tyr Lys Gly Arg Asn Val Val Thr Val Ser Asp His Glu Leu
            980                 985                 990

Phe Lys Ser Asp His Val Leu Leu Pro Pro Pro Gly Leu Ser Pro Ser
        995                 1000                1005

Tyr Ile Phe Gln Lys Val Glu Glu Ser Lys Leu Lys Pro Asn Thr Arg
```

-continued

```
     1010                     1015                     1020

Tyr Ile Val Ser Gly Phe Ile Ala His Gly Lys Asp Leu Glu Ile Val
1025                1030                1935                1040

Val Ser Arg Tyr Gly Gln Glu Val Gln Lys Val Val Gln Val Pro Tyr
                1045                1050                1055

Gly Glu Ala Phe Pro Leu Thr Ser Asn Gly Pro Val Cys Cys Pro Pro
            1060                1065                1070

Arg Ser Thr Ser Asn Gly Thr Leu Gly Asp Pro His Phe Phe Ser Tyr
        1075                1080                1085

Ser Ile Asp Val Gly Ala Leu Asp Leu Gln Ala Asn Pro Gly Ile Glu
    1090                1095                1100

Phe Gly Leu Arg Ile Val Asn Pro Thr Gly Met Ala Arg Val Ser Asn
1105                1110                1115                1120

Leu Glu Ile Arg Glu Asp Arg Pro Leu Ala Ala Asn Glu Ile Ary Gln
                1125                1130                1135

Val Gln Arg Val Ala Arg Asn Trp Arg Thr Glu Tyr Glu Lys Glu Arg
            1140                1145                1150

Ala Glu Val Thr Ser Leu Ile Gln Pro Val Ile Asn Arg Ile Asn Gly
        1155                1160                1165

Leu Tyr Glu Asn Gly Asn Trp Asn Gly Ser Ile Arg Ser Asp Ile Ser
    1170                1175                1180

Tyr Gln Asn Ile Asp Ala Ile Val Leu Pro Thr Leu Pro Lys Leu Arg
1185                1190                1195                1290

His Trp Phe Met Ser Asp Arg Phe Ser Glu Gln Gly Asp Ile Met Ala
                1205                1210                1215

Lys Phe Gln Gly Ala Leu Asn Arg Ala Tyr Ala Gln Leu Glu Gln Ser
            1220                1225                1230

Thr Leu Leu His Asn Gly His Phe Thr Lys Asp Ala Ala Asn Trp Thr
        1235                1240                1245

Ile Glu Gly Asp Ala His Gln Ile Thr Leu Glu Asp gly Arg Arg Val
    1250                1255                1260

Leu Arg Leu Pro Asp Trp Ser Ser Ser Val Ser Gln Met Ile Glu Ile
1265                1230                1275                1280

Glu Asn Phe Asn Pro Asp Lys Glu Tyr Asn Leu Val Phe His Gly Gln
                1285                1290                1295

Gly Glu Gly Thr Val Thr Leu Glu His Gly Glu Glu Thr Lys Tyr Ile
            1300                1305                1310

Glu Thr His Thr His His Phe Ala Asn Phe Thr Thr Ser Gln Arg Gln
        1315                1320                1325

Gly Leu Thr Phe Glu Ser Asn Lys Val Thr Val Thr Ile Ser Ser Glu
    1330                1335                1340

Asp Gly Glu Phe Leu Val Asp Asn Ile Ala Leu Val Glu Ala Pro Leu
1345                1350                1355                1360

Pro Thr Asp Asp Gln Asn Ser Glu Gly Asn Thr Ala Ser Ser Thr Asn
                1365                1370                1375

Ser Asp Thr Ser Met Asn Asn Asn Gln
            1380                1385
```

( 2 ) INFORMATION FOR SEQ ID NO:3:

( i ) SEQUENCE CHARACTERISTICS:
( A ) LENGTH: 3867 base airs
( B ) TYPE: nucleic acid
( C ) STRANDEDNESS: double
( D ) TOPOLOGY: linear ( i i ) MOLECULE TYPE: DNA (genomic)

-continued ( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: PS17
( C ) INDIVIDUAL ISOLATE: PS17b ( v i i ) IMMEDIATE SOURCE:
( B ) CLONE: E. coli NM522(pMYC 1628) NRRL B-18652

( x i ) SEQUENCE DESCRIPTION: SEQ ID NO:3:

```
ATGGCAATTT TAAATGAATT ATATCCATCT GTACCTTATA ATGTATTGGC GTATACGCCA   60
CCCTCTTTTT TACCTGATGC GGGTACACAA GCTACACCTG CTGACTTAAC AGCTTATGAA  120
CAATTGTTGA AAAATTTAGA AAAAGGGATA AATGCTGGAA CTTATTCGAA AGCAATAGCT  180
GATGTACTTA AAGGTATTTT TATAGATGAT ACAATAAATT ATCAAACATA TGTAAATATT  240
GGTTTAAGTT TAATTACATT AGCTGTACCG GAAATTGGTA TTTTTACACC TTTCATCGGT  300
TTGTTTTTTG CTGCATTGAA TAAACATGAT GCTCCACCTC CTCCTAATGC AAAAGATATA  360
TTTGAGGCTA TGAAACCAGC GATTCAAGAG ATGATTGATA GAACTTTAAC TGCGGATGAG  420
CAAACATTTT TAAATGGGGA AATAAGTGGT TTACAAAATT TAGCAGCAAG ATACCAGTCT  480
ACAATGGATG ATATTCAAAG CCATGGAGGA TTTAATAAGG TAGATTCTGG ATTAATTAAA  540
AAGTTTACAG ATGAGGTACT ATCTTTAAAT AGTTTTTATA CAGATCGTTT ACCTGTATTT  600
ATTACAGATA ATACAGCGGA TCGAACTTTG TTAGGTCTTC CTTATTATGC TATACTTGCG  660
AGCATGCATC TTATGTTATT AAGAGATATC ATTACTAAGG GTCCGACATG GGATTCTAAA  720
ATTAATTTCA CACCAGATGC AATTGATTCC TTTAAAACCG ATATTAAAAA TAATATAAAG  780
CTTTACTCTA AAACTATTTA TGACGTATTT CAGAAGGGAC TTGCTTCATA CGGAACGCCT  840
TCTGATTTAG AGTCCTTTGC AAAAAAACAA AAATATATTG AAATTATGAC AACACATTGT  900
TTAGATTTTG CAAGATTGTT TCCTACTTTT GATCCAGATC TTTATCCAAC AGGATCAGGT  960
GATATAAGTT TACAAAAAAC ACGTAGAATT CTTTCTCCTT TTATCCCTAT ACGTACTGCA 1020
GATGGGTTAA CATTAAATAA TACTTCAATT GATACTTCAA ATTGGCCTAA TTATGAAAAT 1080
GGGAATGGCG CGTTTCCAAA CCCAAAAGAA AGAATATTAA AACAATTCAA ACTGTATCCT 1140
AGTTGGAGAG CGGCACAGTA CGGTGGGCTT TTACAACCTT ATTTATGGGC AATAGAAGTC 1200
CAAGATTCTG TAGAGACTCG TTTGTATGGG CAGCTTCCAG CTGTAGATCC ACAGGCAGGG 1260
CCTAATTATG TTTCCATAGA TTCTTCTAAT CCAATCATAC AAATAAATAT GGATACTTGG 1320
AAAACACCAC CACAAGGTGC GAGTGGGTGG AATACAAATT TAATGAGAGG AAGTGTAAGC 1380
GGGTTAAGTT TTTTACAACG AGATGGTACG AGACTTAGTG CTGGTATGGG TGGTGGTTTT 1440
GCTGATACAA TATATAGTCT CCCTGCAACT CATTATCTTT CTTATCTCTA TGGAACTCCT 1500
TATCAAACTT CTGATAACTA TTCTGGTCAC GTTGGTGCAT TGGTAGGTGT GAGTACGCCT 1560
CAAGAGGCTA CTCTTCCTAA TATTATAGGT CAACCAGATG AACAGGGAAA TGTATCTACA 1620
ATGGGATTTC CGTTTGAAAA AGCTTCTTAT GGAGGTACAG TTGTTAAAGA ATGGTTAAAT 1680
GGTGCGAATG CGATGAAGCT TTCTCCTGGG CAATCTATAG GTATTCCTAT TACAAATGTA 1740
ACAAGTGGAG AATATCAAAT TCGTTGTCGT TATGCAAGTA ATGATAATAC TAACGTTTTC 1800
TTTAATGTAG ATACTGGTGG AGCAAATCCA ATTTTCCAAC AGATAAACTT TGCATCTACT 1860
GTAGATAATA ATACGGGAGT ACAAGGAGCA AATGGTGTCT ATGTAGTCAA ATCTATTGCT 1920
ACAACTGATA ATTCTTTTAC AGTAAAAATT CCTGCGAAGA CGATTAATGT TCATTTAACC 1980
AACCAAGGTT CTTCTGATGT CTTTTTAGAT CGTATTGAGT TTGTTCCAAT TCTAGAATCA 2040
```

-continued

```
AATACTGTAA CTATATTCAA CAATTCATAT ACTACAGGTT CAGCAAATCT TATACCAGCA 2100
ATAGCTCCTC TTTGGAGTAC TAGTTCAGAT AAAGCCCTTA CAGGTTCTAT GTCAATAACA 2160
GGTCGAACTA CCCCTAACAG TGATGATGCT TTGCTTCGAT TTTTTAAAAC TAATTATGAT 2220
ACACAAACCA TTCCTATTCC GGGTTCCGGA AAAGATTTTA CAAATACTCT AGAAATACAA 2280
GACATAGTTT CTATTGATAT TTTTGTCGGA TCTGGTCTAC ATGGATCCGA TGGATCTATA 2340
AAATTAGATT TTACCAATAA TAATAGTGGT AGTGGTGGCT CTCCAAAGAG TTTCACCGAG 2400
CAAAATGATT TAGAGAATAT CACAACACAA GTGAATGCTC TATTCACATC TAATACACAA 2460
GATGCACTTG CAACAGATGT GAGTGATCAT GATATTGAAG AAGTGGTTCT AAAAGTAGAT 2520
GCATTATCTG ATGAAGTGTT TGGAAAAGAG AAAAAAACAT TGCGTAAATT TGTAAATCAA 2580
GCGAAGCGCT TAAGCAAGGC GCGTAATCTC CTGGTAGGAG GCAATTTTGA TAACTTGGAT 2640
GCTTGGTATA GAGGAAGAAA TGTAGTAAAC GTATCTAATC ACGAACTGTT GAAGAGTGAT 2700
CATGTATTAT TACCACCACC AGGATTGTCT CCATCTTATA TTTTCCAAAA AGTGGAGGAA 2760
TCTAAATTAA AACGAAATAC ACGTTATACG GTTTCTGGAT TTATTGCGCA TGCAACAGAT 2820
TTAGAAATTG TGGTTTCTCG TTATGGGCAA GAAATAAAGA AAGTGGTGCA AGTTCCTTAT 2880
GGAGAAGCAT TCCCATTAAC ATCAAGTGGA CCAGTTTGTT GTATCCCACA TTCTACAAGT 2940
AATGGAACTT TAGGCAATCC ACATTTCTTT AGTTACAGTA TTGATGTAGG TGCATTAGAT 3000
GTAGACACAA ACCCTGGTAT TGAATTCGGT CTTCGTATTG TAAATCCAAC TGGAATGGCA 3060
CGCGTAAGCA ATTTGGAAAT TCGTGAAGAT CGTCCATTAG CAGCAAATGA AATACGACAA 3120
GTACAACGTG TCGCAAGAAA TTGGAGAACC GAGTATGAGA AAGAACGTGC GGAAGTAACA 3180
AGTTTAATTC AACCTGTTAT CAATCGAATC AATGGATTGT ATGACAATGG AAATTGGAAC 3240
GGTTCTATTC GTTCAGATAT TTCGTATCAG AATATAGACG CGATTGTATT ACCAACGTTA 3300
CCAAAGTTAC GCCATTGGTT TATGTCAGAT AGATTTAGTG AACAAGGAGA TATCATGGCT 3360
AAATTCCAAG GTGCATTAAA TCGTGCGTAT GCACAACTGG AACAAAATAC GCTTCTGCAT 3420
AATGGTCATT TTACAAAAGA TGCAGCCAAT TGGACGGTAG AAGGCGATGC ACATCAGGTA 3480
GTATTAGAAG ATGGTAAACG TGTATTACGA TTGCCAGATT GGTCTTCGAG TGTGTCTCAA 3540
ACGATTGAAA TCGAGAATTT TGATCCAGAT AAAGAATATC AATTAGTATT TCATGGGCAA 3600
GGAGAAGGAA CGGTTACGTT GGAGCATGGA GAAGAAACAA AATATATAGA AACGCATACA 3660
CATCATTTTG CGAATTTTAC AACTTCTCAA CGTCAAGGAC TCACGTTTGA ATCAAATAAA 3720
GTGACAGTGA CCATTTCTTC AGAAGATGGA GAATTCTTAG TGGATAATAT TGCGCTTGTG 3780
GAAGCTCCTC TTCCTACAGA TGACCAAAAT TCTGAGGGAA ATACGGCTTC CAGTACGAAT 3840
AGCGATACAA GTATGAACAA CAATCAA 3867
```

( 2 ) INFORMATION FOR SEQ ID NO:4:

( i ) SEQUENCE CHARACTERISTICS:

( A ) LENGTH: 1289 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:

( A ) ORGANISM: BACILLUS THURINGIENSIS
( C ) INDIVIDUAL ISOLATE: PS17

( v i i ) IMMEDIATE SOURCE:

( B ) CLONE: E. coli NM522(pMYC 1628) NRRL B-18652

-continued ( x i ) SEQUENCE DESCRIPTION: SEQ ID NO:4:

```
Met Ala Ile Leu Asn Glu Leu Tyr Pro Ser Val Pro Tyr Asn Val Leu
1               5                   10                  15

Ala Tyr Thr Pro Pro Ser Phe Leu Pro Asp Ala Gly Thr Gln Ala Thr
            20                  25                  30

Pro Ala Asp Leu Thr Ala Tyr Glu Gln Leu Leu Lys Asn Leu Glu Lys
        35                  40                  45

Gly Ile Asn Ala Gly Thr Tyr Ser Lys Ala Ile Ala Asp Val Leu Lys
    50                  55                  60

Gly Ile Phe Ile Asp Asp Thr Ile Asn Tyr Gln Thr Tyr Val Asn Ile
65                  70                  75                  80

Gly Leu Ser Leu Ile Thr Leu Ala Val Pro Glu Ile Gly Ile Phe Thr
                85                  90                  95

Pro Phe Ile Gly Leu Phe Phe Ala Ala Leu Asn Lys His Asp Ala Pro
            100                 105                 110

Pro Pro Pro Asn Ala Lys Asp Ile Phe Glu Ala Met Lys Pro Ala Ile
        115                 120                 115

Gln Glu Met Ile Asp Arg Thr Leu Thr Ala Asp Glu Gln Thr Phe Leu
    130                 135                 140

Asn Gly Glu Ile Ser Gly Leu Gln Asn Leu Ala Ala Arg Tyr Gln Ser
145                 150                 155                 160

Thr Met Asp Asp Ile Gln Ser His Gly Gly Phe Asn Lys Val Arg Ser
                165                 170                 175

Gly Leu Ile Lys Lys Phe Thr Asp Glu Val Leu Ser Leu Asn Ser Phe
            180                 185                 190

Tyr Thr Asp Arg Leu Pro Val Phe Ile Thr Asp Asn Thr Ala Asp Arg
        195                 200                 205

Thr Leu Leu Gly Leu Pro Tyr Tyr Ala Ile Leu Ala Ser Met His Leu
    210                 215                 220

Met Leu Leu Arg Asp Ile Ile Thr Lys Gly Pro Thr Trp Asp Ser Lys
225                 230                 235                 240

Ile Asn Phe Thr Pro Asp Ala Ile Asp Ser Phe Lys Thr Asp Ile Lys
                245                 250                 255

Asn Asn Ile Lys Leu Tyr Ser Lys Thr Ile Tyr Asp Val Phe Gln Lys
            260                 265                 270

Gly Leu Ala Ser Tyr Gly Thr Pro Ser Asp Leu Glu Ser Phe Ala Lys
        275                 280                 285

Lys Gln Lys Tyr Ile Glu Ile Met Thr Thr His Cys Leu Asp Phe Ala
    290                 295                 300

Arg Leu Phe Pro Thr Phe Asp Pro Asp Leu Tyr Pro Thr Gly Ser Gly
305                 310                 315                 320

Asp Ile Ser Leu Gln Lys Thr Arg Arg Ile Leu Ser Pro Phe Ile Pro
                325                 330                 335

Ile Arg Thr Ala Asp Gly Leu Thr Leu Asn Asn Thr Ser Ile Asp Thr
            340                 345                 350

Ser Asn Trp Pro Asn Tyr Glu Asn Gly Asn Gly Ala Phe Pro Asn Pro
        355                 360                 365

Lys Glu Arg Ile Leu Lys Gln Phe Lys Leu Tyr Pro Ser Trp Arg Ala
    370                 375                 380

Ala Gln Tyr Gly Gly Leu Leu Gln Pro Tyr Leu Trp Ala Ile Glu Val
385                 390                 395                 400

Gln Asp Ser Val Glu Thr Arg Leu Tyr Gly Gln Leu Pro Ala Val Asp
                405                 410                 415

Pro Gln Ala Gly Pro Asn Tyr Val Ser Ile Asp Ser Ser Asn Pro Ile
```

-continued 429 425 430

Ile Gln Ile Asn Met Asp Thr Trp Lys Thr Pro Pro Gln Gly Ala Ser
435 440 445

Gly Trp Asn Thr Asn Leu Met Arg Gly Ser Val Ser Gly Leu Ser Phe
450 455 460

Leu Gln Arg Asp Gly Thr Arg Leu Ser Ala Gly Met Gly Gly Gly Phe
465 470 475 480

Ala Asp Thr Ile Tyr Ser Leu Pro Ala Thr His Tyr Leu Ser Tyr Leu
485 490 495

Tyr Gly Thr Pro Tyr Gln Thr Ser Asp Asn Tyr Ser Gly His Val Gly
500 505 510

Ala Leu Val Gly Val Ser Thr Pro Gln Glu Ala Thr Leu Pro Asn Ile
515 520 525

Ile Gly Gln Pro Asp Glu Gln Gly Asn Val Ser Thr Met Gly Phe Pro
533 535 540

Phe Glu Lys Ala Ser Tyr Gly Gly Thr Val Val Lys Glu Trp Leu Asn
545 550 555 560

Gly Ala Asn Ala Met Lys Leu Ser Pro Gly Gln Ser Ile Gly Ile Pro
565 570 575

Ile Thr Asn Val Thr Ser Gly Glu Tyr Gln Ile Arg Cys Arg Tyr Ala
580 585 590

Ser Asn Asp Asn Thr Asn Val Phe Phe Asn Val Asp Thr Gly Gly Ala
595 600 605

Asn Pro Ile Phe Gln Gln Ile Asn Phe Ala Ser Thr Val Asp Asn Asn
610 615 620

Thr Gly Val Gln Gly Ala Asn Gly Val Tyr Val Val Lys Ser Ile Ala
625 630 635 640

Thr Thr Asp Asn Ser Phe Thr Val Lys Ile Pro Ala Lys Thr Ile Asn
645 650 655

Val His Leu Thr Asn Gln Gly Ser Ser Asp Val Phe Leu Asp Arg Ile
660 665 670

Glu Phe Val Pro Ile Leu Glu Ser Asn Thr Val Thr Ile Phe Asn Asn
675 680 685

Ser Tyr Thr Thr Gly Ser Ala Asn Leu Ile Pro Ala Ile Ala Pro Leu
690 695 700

Trp Ser Thr Ser Ser Asp Lys Ala Leu Thr Gly Ser Met Ser Ile Thr
705 710 715 720

Gly Arg Thr Thr Pro Asn Ser Asp Asp Ala Leu Leu Arg Phe Phe Lys
725 730 735

Thr Asn Tyr Asp Thr Gln Thr Ile Pro Ile Pro Gly Ser Gly Lys Asp
740 745 750

Phe Thr Asn Thr Leu Glu Ile Gln Asp Ile Val Ser Ile Asp Ile Phe
755 760 765

Val Glg Ser Gly Leu His Gly Ser Asp Gly Ser Ile Lys Leu Asp Phe
770 775 780

Thr Asn Asn Asn Ser Gly Ser Gly Gly Ser Pro Lys Ser Phe Thr Glu
785 790 795 800

Gln Asn Asp Leu Glu Asn Ile Thr Thr Gln Val Asn Ala Leu Phe Thr
805 810 815

Ser Asn Thr Gln Asp Ala Leu Ala Thr Asp Val Ser Asp His Asp Ile
820 825 830

Glu Glu Val Val Leu Lys Val Asp Ala Leu Ser Asp Glu Val Phe Gly
835 840 845

Lys Glu Lys Lys Thr Leu Arg Lys Phe Val Asn Gln Ala Lys Arg Leu
850 855 860

-continued

Ser Lys Ala Arg Asn Leu Leu Val Gly Gly Asn Phe Asp Asn Leu Asp
865 870 875 880

Ala Trp Tyr Arg Gly Arg Asn Val Val Asn Val Ser Asn His Glu Leu
885 890 895

Leu Lys Ser Asp His Val Leu Leu Pro Pro Pro Gly Leu Ser Pro Ser
900 905 910

Tyr Ile Phe Gln Lys Val Glu Glu Ser Lys Leu Lys Arg Asn Thr Arg
915 920 925

Tyr Thr Val Ser Gly Phe Ile Ala His Ala Thr Asp Leu Glu Ile Val
930 935 940

Val Ser Arg Tyr Gly Gln Glu Ile Lys Lys Val Val Gln Val Pro Tyr
945 950 955 960

Gly Glu Ala Phe Pro Leu Thr Ser Ser Gly Pro Val Cys Cys Ile Pro
965 979 975

His Ser Thr Ser Asn Gly Thr Leu Gly Asn Pro His Phe Phe Ser Tyr
980 985 990

Ser Ile Asp Val Gly Ala Leu Asp Val Asp Thr Asn Pro Gly Ile Glu
995 1000 1005

Phe Gly Leu Arg Ile Val Asn Pro Thr Gly Met Ala Arg Val Ser Asn
1010 1015 1020

Leu Glu Ile Arg Glu Asp Arg Pro Leu Ala Ala Asn Glu Ile Arg Gln
1025 1030 1035 1040

Val Gln Arg Val Ala Arg Asn Trp Arg Thr Glu Tyr Glu Lys Glu Arg
1045 1050 1055

Ala Glu Val Thr Ser Leu Ile Gln Pro Val Ile Asn Arg Ile Asn Gly
1060 1065 1070

Leu Tyr Asp Asn Gly Asn Trp Asn Gly Ser Ile Arg Ser Asp Ile Ser
1035 1080 1085

Tyr Gln Asn Ile Asp Ala Ile Val Leu Pro Thr Leu Pro Lys Leu Arg
1090 1095 1100

His Trp Phe Met Ser Asp Arg Phe Ser Glu Gln Gly Asp Ile Met Ala
1105 1110 1115 1120

Lys Phe Gln Gly Ala Leu Asn Arg Ala Tyr Ala Gln Leu Glu Gln Asn
1125 1130 1135

Thr Leu Leu His Asn Gly His Phe Thr Lys Asp Ala Ala Asn Trp Thr
1140 1145 1150

Val Glu Gly Asp Ala His Gln Val Val Leu Glu Asp Gly Lys Arg Val
1155 1160 1165

Leu Arg Leu Pro Asp Trp Ser Ser Ser Val Ser Gln Thr Ile Glu Ile
1150 1175 1180

Glu Asn Phe Asp Pro Asp Lys Glu Tyr Gln Leu Val Phe His Gly Gln
1185 1190 1195 1200

Gly Glu Gly Thr Val Thr Leu Glu His Gly Glu Glu Thr Lys Tyr Ile
1205 1210 1215

Glu Thr His Thr His His Phe Ala Asn Phe Thr Thr Ser Gln Arg Gln
1220 1225 1230

Gly Leu Thr Phe Glu Ser Asn Lys Val Thr Val Thr Ile Ser Ser Glu
1235 1240 1245

Asp Gly Glu Phe Leu Val Asp Asn Ile Ala Leu Val Glu Ala Pro Leu
1250 1255 1260

Pro Thr Asp Asp Gln Asn Ser Glu Gly Asn Thr Ala Ser Ser Thr Asn
1265 1270 1275 1280

Ser Asp Thr Ser Met Asn Asn Asn Gln
1285

-continued ( 2 ) INFORMATION FOR SEQ ID NO:5:

( i ) SEQUENCE CHARACTERISTICS:
( A ) LENGTH: 3771 base airs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( C ) INDIVIDUAL ISOLATE: 33f2

( v i i ) IMMEDIATE SOURCE:
( B ) CLONE: E. coli NM522(pMYC 2316) B-18785

( i x ) FEATURE:
( A ) NAME/KEY: misc feature
( B ) LOCATION: 4..24
( D ) OTHER INFORMATION: /function="oligonucleotide hybridization probe"
/ product="GCA/T ACA/T TTA AAT GAA GTA/T TAT"
/ standard name="probe a"
/ note="Probe A"

( i x ) FEATURE:
( A ) NAME/KEY: misc feature
( B ) LOCATION: 13..33
( D ) OTHER INFORMATION: /function="oligonucleotide hybridization probe"
/ product="AAT GAA GTA/T TAT CCA/T GTA/T AAT"
/ standard name="Probe B"
/ label=probe-b
/ note="probe b"

( x i ) SEQUENCE DESCRIPTION: SEQ ID NO:5:

ATGGCTACAC TTAATGAAGT ATATCCTGTG AATTATAATG TATTATCTTC TGATGCTTTT 60

CAACAATTAG ATACAACAGG TTTTAAAAGT AAATATGATG AAATGATAAA AGCATTCGAA 120

AAAAAATGGA AAAAAGGGGC AAAAGGAAAA GACCTTTTAG ATGTTGCATG GACTTATATA 180

ACTACAGGAG AAATTGACCC TTTAAATGTA ATTAAAGGTG TTTTATCTGT ATTAACTTTA 240

ATTCCTGAAG TTGGTACTGT GGCCTCTGCA GCAAGTACTA TTGTAAGTTT TATTTGGCCT 300

AAAATATTTG GAGATAAACC AAATGCAAAA AATATATTTG AAGAGCTCAA GCCTCAAATT 360

GAAGCATTAA TTCAACAAGA TATAACAAAC TATCAAGATG CAATTAATCA AAAAAAATTT 420

GACAGTCTTC AGAAAACAAT TAATCTATAT ACAGTAGCTA TAGATAACAA TGATTACGTA 480

ACAGCAAAAA CGCAACTCGA AAATCTAAAT TCTATACTTA CCTCAGATAT CTCCATATTT 540

ATTCCAGAAG GATATGAAAC TGGAGGTTTA CCTTATTATG CTATGGTTGC TAATGCTCAT 600

ATATTATTGT TAAGAGACGC TATAGTTAAT GCAGAGAAAT TAGGCTTTAG TGATAAAGAA 660

GTAGACACAC ATAAAAAATA TATCAAAATG ACAATACACA ATCATACTGA AGCAGTAATA 720

AAAGCATTCT TAAATGGACT TGACAAATTT AAGAGTTTAG ATGTAAATAG CTATAATAAA 780

AAAGCAAATT ATATTAAAGG TATGACAGAA ATGGTTCTTG ATCTAGTTGC TCTATGGCCA 840

ACTTTCGATC CAGATCATTA TCAAAAAGAA GTAGAAATTG AATTTACAAG AACTATTTCT 900

TCTCCAATTT ACCAACCTGT ACCTAAAAAC ATGCAAAATA CCTCTAGCTC TATTGTACCT 960

AGCGATCTAT TTCACTATCA AGGAGATCTT GTAAAATTAG AATTTTCTAC AAGAACGGAC 1020

AACGATGGTC TTGCAAAAAT TTTTACTGGT ATTCGAAACA CATTCTACAA ATCGCCTAAT 1080

ACTCATGAAA CATACCATGT AGATTTTAGT TATAATACCC AATCTAGTGG TAATATTTCA 1140

AGAGGCTCTT CAAATCCGAT TCCAATTGAT CTTAATAATC CCATTATTTC AACTTGTATT 1200

-continued

```
AGAAATTCAT TTTATAAGGC AATAGCGGGA TCTTCTGTTT TAGTTAATTT TAAAGATGGC 1260
ACTCAAGGGT ATGCATTTGC CCAAGCACCA ACAGGAGGTG CCTGGGACCA TTCTTTTATT 1320
GAATCTGATG GTGCCCCAGA AGGGCATAAA TTAAACTATA TTTATACTTC TCCAGGTGAT 1380
ACATTAAGAG ATTTCATCAA TGTATATACT CTTATAAGTA CTCCAACTAT AAATGAACTA 1440
TCAACAGAAA AAATCAAAGG CTTTCCTGCG GAAAAAGGAT ATATCAAAAA TCAAGGGATC 1500
ATGAAATATT ACGGTAAACC AGAATATATT AATGGAGCTC AACCAGTTAA TCTGGAAAAC 1560
CAGCAAACAT TAATATTCGA ATTTCATGCT TCAAAAACAG CTCAATATAC CATTCGTATA 1620
CGTTATGCCA GTACCCAAGG AACAAAAGGT TATTTTCGTT TAGATAATCA GGAACTGCAA 1680
ACGCTTAATA TACCTACTTC ACACAACGGT TATGTAACCG GTAATATTGG TGAAAATTAT 1740
GATTTATATA CAATAGGTTC ATATACAATT ACAGAAGGTA ACCATACTCT TCAAATCCAA 1800
CATAATGATA AAAATGGAAT GGTTTTAGAT CGTATTGAAT TTGTTCCTAA AGATTCACTT 1860
CAAGATTCAC CTCAAGATTC ACCTCCAGAA GTTCACGAAT CAACAATTAT TTTTGATAAA 1920
TCATCTCCAA CTATATGGTC TTCTAACAAA CACTCATATA GCCATATACA TTTAGAAGGA 1980
TCATATACAA GTCAGGGAAG TTATCCACAC AATTTATTAA TTAATTTATT TCATCCTACA 2040
GACCCTAACA GAAATCATAC TATTCATGTT AACAATGGTG ATATGAATGT TGATTATGGA 2100
AAAGATTCTG TAGCCGATGG GTTAAATTTT AATAAAATAA CTGCTACGAT ACCAAGTGAT 2160
GCTTGGTATA GCGGTACTAT TACTTCTATG CACTTATTTA ATGATAATAA TTTTAAAACA 2220
ATAACTCCTA AATTTGAACT TTCTAATGAA TTAGAAAACA TCACAACTCA AGTAAATGCT 2280
TTATTCGCAT CTAGTGCACA AGATACTCTC GCAAGTAATG TAAGTGATTA CTGGATTGAA 2340
CAGGTCGTTA TGAAAGTCGA TGCCTTATCA GATGAAGTAT TTGGAAAAGA GAAAAAAGCA 2400
TTACGTAAAT TGGTAAATCA AGCAAAACGT CTCAGTAAAA TACGAAATCT TCTCATAGGT 2460
GGTAATTTTG ACAATTTAGT CGCTTGGTAT ATGGGAAAAG ATGTAGTAAA AGAATCGGAT 2520
CATGAATTAT TTAAAAGTGA TCATGTCTTA CTACCTCCCC CAACATTCCA TCCTTCTTAT 2580
ATTTTCCAAA AGGTGGAAGA ATCAAAACTA AAACCAAATA CACGTTATAC TATTTCTGGT 2640
TTTATCGCAC ATGGAGAAGA TGTAGAGCTT GTTGTCTCTC GTTATGGGCA AGAAATACAA 2700
AAAGTGATGC AAGTGCCATA TGAAGAAGCA CTTCCTCTTA CATCTGAATC TAATTCTAGT 2760
TGTTGTGTTC CAAATTTAAA TATAAATGAA ACACTAGCTG ATCCACATTT CTTTAGTTAT 2820
AGCATCGATG TTGGTTCTCT GGAAATGGAA GCGAATCCTG GTATTGAATT TGGTCTCCGT 2880
ATTGTCAAAC CAACAGGTAT GGCACGTGTA AGTAATTTAG AAATTCGAGA AGACCGTCCA 2940
TTAACAGCAA AAGAAATTCG TCAAGTACAA CGTGCAGCAA GAGATTGGAA ACAAAACTAT 3000
GAACAAGAAC GAACAGAGAT CACAGCTATA ATTCAACCTG TTCTTAATCA AATTAATGCG 3060
TTATACGAAA ATGAAGATTG GAATGGTTCT ATTCGTTCAA ATGTTTCCTA TCATGATCTA 3120
GAGCAAATTA TGCTTCCTAC TTTATTAAAA ACTGAGGAAA TAAATTGTAA TTATGATCAT 3180
CCAGCTTTTT TATTAAAAGT ATATCATTGG TTTATGACAG ATCGTATAGG AGAACATGGT 3240
ACTATTTTAG CACGTTTCCA AGAAGCATTA GATCGTGCAT ATACACAATT AGAAAGTCGT 3300
AATCTCCTGC ATAACGGTCA TTTTACAACT GATACAGCGA ATTGGACAAT AGAAGGAGAT 3360
GCCCATCATA CAATCTTAGA AGATGGTAGA CGTGTGTTAC GTTTACCAGA TTGGTCTTCT 3420
AATGCAACTC AAACAATTGA AATTGAAGAT TTTGACTTAG ATCAAGAATA CCAATTGCTC 3480
ATTCATGCAA AAGGAAAAGG TTCCATTACT TTACAACATG GAGAAGAAAA CGAATATGTG 3540
GAAACACATA CTCATCATAC AAATGATTTT ATAACATCCC AAAATATTCC TTTCACTTTT 3600
AAAGGAAATC AAATTGAAGT CCATATTACT TCAGAAGATG GAGAGTTTTT AATCGATCAC 3660
```

-continued

ATTACAGTAA TAGAAGTTTC TAAAACAGAC ACAAATACAA ATATTATTGA AAATTCACCA 3720

ATCAATACAA GTATGAATAG TAATGTAAGA GTAGATATAC CAAGAAGTCT C 3771

( 2 ) INFORMATION FOR SEQ ID NO:6:

( i ) SEQUENCE CHARACTERISTICS:
( A ) LENGTH: 1425 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( C ) INDIVIDUAL ISOLATE: PS52A1

( v i i ) IMMEDIATE SOURCE:
( B ) CLONE: E. coli NH522(pMYC 2321) B-18770

( i x ) FEATURE:
( A ) NAME/KEY: mat peptide
( B ) LOCATION: 1..1425
( D ) OTHER INFORMATION: /product="OPEN READING FRAME OF MATURE PROTEIN"

( x i ) SEQUENCE DESCRIPTION: SEQ ID NO:6:

ATGATTATTG ATAGTAAAAC GACTTTACCT AGACATTCAC TTATTCATAC AATTAAATTA 60

AATTCTAATA AGAAATATGG TCCTGGTGAT ATGACTAATG GAAATCAATT TATTATTTCA 120

AAACAAGAAT GGGCTACGAT TGGAGCATAT ATTCAGACTG GATTAGGTTT ACCAGTAAAT 180

GAACAACAAT TAAGAACACA TGTTAATTTA AGTCAGGATA TATCAATACC TAGTGATTTT 240

TCTCAATTAT ATGATGTTTA TTGTTCTGAT AAAACTTCAG CAGAATGGTG GAATAAAAAT 300

TTATATCCTT TAATTATTAA ATCTGCTAAT GATATTGCTT CATATGGTTT TAAAGTTGCT 360

GGTGATCCTT CTATTAAGAA AGATGGATAT TTTAAAAAAT TGCAAGATGA ATTAGATAAT 420

ATTGTTGATA ATAATTCCGA TGATGATGCA ATAGCTAAAG CTATTAAAGA TTTTAAAGCG 480

CGATGTGGTA TTTTAATTAA AGAAGCTAAA CAATATGAAG AAGCTGCAAA AAATATTGTA 540

ACATCTTTAG ATCAATTTTT ACATGGTGAT CAGAAAAAAT TAGAAGGTGT TATCAATATT 600

CAAAAACGTT TAAAAGAAGT TCAAACAGCT CTTAATCAAG CCCATGGGGA AAGTAGTCCA 660

GCTCATAAAG AGTTATTAGA AAAAGTAAAA AATTTAAAAA CAACATTAGA AAGGACTATT 720

AAAGCTGAAC AAGATTTAGA GAAAAAAGTA GAATATAGTT TTCTATTAGG ACCATTGTTA 780

GGATTTGTTG TTTATGAAAT TCTTGAAAAT ACTGCTGTTC AGCATATAAA AAATCAAATT 840

GATGAGATAA AGAAACAATT AGATTCTGCT CAGCATGATT TGGATAGAGA TGTTAAAATT 900

ATAGGAATGT TAAATAGTAT TAATACAGAT ATTGATAATT TATATAGTCA AGGACAAGAA 960

GCAATTAAAG TTTTCCAAAA GTTACAAGGT ATTTGGGCTA CTATTGGAGC TCAAATAGAA 1020

AATCTTAGAA CAACGTCGTT ACAAGAAGTT CAAGATTCTG ATGATGCTGA TGAGATACAA 1080

ATTGAACTTG AGGACGCTTC TGATGCTTGG TTAGTTGTGG CTCAAGAAGC TCGTGATTTT 1140

ACACTAAATG CTTATTCAAC TAATAGTAGA CAAAATTTAC CGATTAATGT TATATCAGAT 1200

TCATGTAATT GTTCAACAAC AAATATGACA TCAAATCAAT ACAGTAATCC AACAACAAAT 1260

ATGACATCAA ATCAATATAT GATTTCACAT GAATATACAA GTTTACCAAA TAATTTTATG 1320

TTATCAAGAA ATAGTAATTT AGAATATAAA TGTCCTGAAA ATAATTTTAT GATATATTGG 1380

TATAATAATT CGGATTGGTA TAATAATTCG GATTGGTATA ATAAT 1425

-continued ( 2 ) INFORMATION FOR SEQ ID NO:7 (PS52A1):

( i ) SEQUENCE CHARACTERISTICS:
( A ) LENGTH: 475 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS52A1

( v i i ) IMMEDIATE SOURCE:
( B ) CLONE: E. coli NM522(pMYC 2321) B-18770

( i x ) FEATURE:
( A ) NAME/KEY: Protein
( B ) LOCATION: 1..475

( x i ) SEQUENCE DESCRIPTION: SEQ ID NO:7:

| | | | | | | | | | | | | | | | |
|---|---|---|---|---|---|---|---|---|---|---|---|---|---|---|---|
| Met | Ile | Ile | Asp | Ser | Lys | Thr | Thr | Leu | Pro | Arg | His | Ser | Leu | Ile | His |
| 1 | | | | 5 | | | | | 10 | | | | | | 15 |
| Thr | Ile | Lys | Leu | Asn | Ser | Asn | Lys | Lys | Tyr | Gly | Pro | Gly | Asp | Met | Thr |
| | | | 20 | | | | | 25 | | | | | 30 | | |
| Asn | Gly | Asn | Gln | Phe | Ile | Ile | Ser | Lys | Gln | Glu | Trp | Ala | Thr | Ile | Gly |
| | | 35 | | | | | 40 | | | | | 45 | | | |
| Ala | Tyr | Ile | Gln | Thr | Gly | Leu | Gly | Leu | Pro | Val | Asn | Glu | Gln | Gln | Leu |
| | 50 | | | | | 55 | | | | | 60 | | | | |
| Arg | Thr | His | Val | Asn | Leu | Ser | Gln | Asp | Ile | Ser | Ile | Pro | Ser | Asp | Phe |
| 65 | | | | | 70 | | | | | 75 | | | | | |
| Ser | Gln | Leu | Tyr | Asp | Val | Tyr | Cys | Ser | Asp | Lys | Thr | Ser | Ala | Glu | Trp |
| | | | | 85 | | | | | 90 | | | | | 95 | |
| Trp | Asn | Lys | Asn | Leu | Tyr | Pro | Leu | Ile | Ile | Lys | Ser | Ala | Asn | Asp | Ile |
| | | | 100 | | | | | 105 | | | | | 110 | | |
| Ala | Ser | Tyr | Gly | Phe | Lys | Val | Ala | Gly | Asp | Pro | Ser | Ile | Lys | Lys | Asp |
| | | 115 | | | | | 120 | | | | | 125 | | | |
| Gly | Tyr | Phe | Lys | Lys | Leu | Gln | Asp | Glu | Leu | Asp | Asn | Ile | Val | Asp | Asn |
| | 130 | | | | | 135 | | | | | 140 | | | | |
| Asn | Ser | Asp | Asp | Asp | Ala | Ile | Ala | Lys | Ala | Ile | Lys | Asp | Phe | Lys | Ala |
| 145 | | | | | 150 | | | | | 155 | | | | | 160 |
| Arg | Cys | Gly | Ile | Leu | Ile | Lys | Glu | Ala | Lys | Gln | Tyr | Glu | Glu | Ala | Ala |
| | | | | 165 | | | | | 170 | | | | | 175 | |
| Lys | Asn | Ile | Val | Thr | Ser | Leu | Asp | Gln | Phe | Leu | His | Gly | Asp | Gln | Lys |
| | | | 180 | | | | | 185 | | | | | 190 | | |
| Lys | Leu | Glu | Gly | Val | Ile | Asn | Ile | Gln | Lys | Arg | Leu | Lys | Glu | Val | Gln |
| | | 195 | | | | | 200 | | | | | 205 | | | |
| Thr | Ala | Leu | Asn | Gln | Ala | His | Gly | Glu | Ser | Ser | Pro | Ala | His | Lys | Glu |
| | 210 | | | | | 215 | | | | | 220 | | | | |
| Leu | Leu | Glu | Lys | Val | Lys | Asn | Leu | Lys | Thr | Thr | Leu | Glu | Arg | Thr | Ile |
| 225 | | | | | 210 | | | | | 235 | | | | | 240 |
| Lys | Ala | Glu | Gln | Asp | Leu | Glu | Lys | Lys | Val | Glu | Tyr | Ser | Phe | Leu | Leu |
| | | | | 245 | | | | | 250 | | | | | 255 | |
| Gly | Pro | Leu | Leu | Gly | Phe | Val | Val | Tyr | Glu | Ile | Leu | Glu | Asn | Thr | Ala |
| | | | 260 | | | | | 265 | | | | | 270 | | |
| Val | Gln | His | Ile | Lys | Asn | Gln | Ile | Asp | Glu | Ile | Lys | Lys | Gln | Leu | Asp |
| | | 275 | | | | | 280 | | | | | 285 | | | |
| Ser | Ala | Gln | His | Asp | Leu | Asp | Arg | Asp | Val | Lys | Ile | Ile | Gly | Met | Leu |

-continued 290 295 300

Asn Ser Ile Asn Thr Asp Ile Asp Asn Leu Tyr Ser Gln Gly Gln Glu
305 310 315 320

Ala Ile Lys Val Phe Gln Lys Leu Gln Gly Ile Trp Ala Thr Ile Gly
325 330 335

Ala Gln Ile Glu Asn Leu Arg Thr Thr Ser Leu Gln Glu Val Gln Asp
340 345 350

Ser Asp Asp Ala Asp Glu Ile Gln Ile Glu Leu Glu Asp Ala Ser Asp
355 360 365

Ala Trp Leu Val Val Ala Gln Glu Ala Arg Asp Phe Thr Leu Asn Ala
370 375 380

Tyr Ser Thr Asn Ser Arg Gln Asn Leu Pro Ile Asn Val Ile Ser Asp
315 390 395 400

Ser Cys Asn Cys Ser Thr Thr Asn Met Thr Ser Asn Gln Tyr Ser Asn
405 410 415

Pro Thr Thr Asn Met Thr Ser Asn Gln Tyr Met Ile Ser His Glu Tyr
420 425 430

Thr Ser Leu Pro Asn Asn Phe Met Leu Ser Arg Asn Ser Asn Leu Glu
435 440 445

Tyr Lys Cys Pro Glu Asn Asn Phe Met Ile Tyr Trp Tyr Asn Asn Ser
450 455 460

Asp Trp Tyr Asn Asn Ser Asp Trp Tyr Asn Asn
465 470 475

( 2 ) INFORMATION FOR SEQ ID NO:8:

( i ) SEQUENCE CHARACTERISTICS:
( A ) LENGTH: 1185 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI- SENSE: NO ( v i ) ORIGINAL SOURCE:
( A ) ORGANISM: BACILLUS THURINGIENSIS
( C ) INDIVIDUAL ISOLATE: PS69D1

( v i i ) IMMDIATE SOURCE:
( B ) CLONE: E. coli NM522(pMYC2317) NRRL B- 18816

( i x ) FEATURE:
( A ) NAME/KEY: mat peptide
( B ) LOCATION: 1..1185

( x i ) SEQUENCE DESCRIPTION: SEQ ID NO:8:

ATGATTTTAG GGAATGGAAA GACTTTACCA AAGCATATAA GATTAGCTCA TATTTTTGCA 60

ACACAGAATT CTTCAGCTAA GAAAGACAAT CCTCTTGGAC CAGAGGGGAT GGTTACTAAA 120

GACGGTTTTA TAATCTCTAA GGAAGAATGG GCATTTGTGC AGGCCTATGT GACTACAGGC 180

ACTGGTTTAC CTATCAATGA CGATGAGATG CGTAGACATG TTGGGTTACC ATCACGCATT 240

CAAATTCCTG ATGATTTTAA TCAATTATAT AAGGTTTATA ATGAAGATAA ACATTTATGC 300

AGTTGGTGGA ATGGTTTCTT GTTTCCATTA GTTCTTAAAA CAGCTAATGA TATTTCCGCT 360

TACGGATTTA AATGTGCTGG AAAGGGTGCC ACTAAAGGAT ATTATGAGGT CATGCAAGAC 420

GATGTAGAAA ATATTTCAGA TAATGGTTAT GATAAAGTTG CACAAGAAAA AGCACATAAG 480

GATCTGCAGG CGCGTTGTAA AATCCTTATT AAGGAGGCTG ATCAATATAA AGCTGCAGCG 540

GATGATGTTT CAAAACATTT AAACACATTT CTTAAAGGCG GTCAAGATTC AGATGGCAAT 600

-continued

GATGTTATTG GCGTAGAGGC TGTTCAAGTA CAACTAGCAC AAGTAAAAGA TAATCTTGAT 660

GGCCTATATG GCGACAAAAG CCCAAGACAT GAAGAGTTAC TAAAGAAAGT AGACGACCTG 720

AAAAAAGAGT TGGAAGCTGC TATTA&AGCA GAGAATGAAT TAGAAAAGAA AGTGAAAATG 780

AGTTTTGCTT TAGGACCATT ACTTGGATTT GTTGTATATG AAATCTTAGA GCTAACTGCG 840

GTCAAAAGTA TACACAAGAA AGTTGAGGCA CTACAAGCCG AGCTTGACAC TGCTAATGAT 900

GAACTCGACA GAGATGTAAA AATCTTAGGA ATGATGAATA GCATTGACAC TGATATTGAC 960

AACATGTTAG AGCAAGGTGA GCAAGCTCTT GTTGTATTTA GAAAAATTGC AGGCATTTGG 1020

AGTGTTATAA GTCTTAATAT CGGCAATCTT CGAGAAACAT CTTTAAAAGA GATAGAAGAA 1080

GAAAATGATG ACGATGCACT GTATATTGAG CTTGGTGATG CCGCTGGTCA ATGGAAAGAG 1140

ATAGCCGAGG AGGCACAATC CTTTGTACTA AATGCTTATA CTCCT 1185

( 2 ) INFORMATION FOR SEQ ID NO:9:

( i ) SEQUENCE CHARACTERISTICS:
( A ) LENGTH: 395 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS69D1

( v i i ) IMMEDIATE SOURCE:
( B ) CLONE: E. coli NM522(pMYC2317) NRRL B-18816

( i x ) FEATURE:
( A ) NAME/KEY: Protein
( B ) LOCATION: 1..395

( x i ) SEQUENCE DESCRIPTION: SEQ ID NO:9:

```
Met Ile Leu Gly Asn Gly Lys Thr Leu Pro Lys His Ile Arg Leu Ala
1               5                   10                  15

His Ile Phe Ala Thr Gln Asn Ser Ser Ala Lys Lys Asp Asn Pro Leu
            20                  25                  30

Gly Pro Glu Gly Met Val Thr Lys Asp Gly Phe Ile Ile Ser Lys Glu
        35                  40                  45

Glu Trp Ala Phe Val Gln Ala Tyr Val Thr Thr Gly Thr Gly Leu Pro
    50                  55                  60

Ile Asn Asp Asp Glu Met Arg Arg His Val Gly Leu Pro Ser Arg Ile
65                  70                  75                  80

Gln Ile Pro Asp Asp Phe Asn Gln Leu Tyr Lys Val Tyr Asn Glu Asp
                85                  90                  95

Lys His Leu Cys Ser Trp Trp Asn Gly Phe Leu Phe Pro Leu Val Leu
            100                 105                 110

Lys Thr Ala Asn Asp Ile Ser Ala Tyr Gly Phe Lys Cys Ala Gly Lys
        115                 120                 125

Gly Ala Thr Lys Gly Tyr Tyr Glu Val Met Gln Asp Asp Val Glu Asn
    130                 135                 140

Ile Ser Asp Asn Gly Tyr Asp Lys Val Ala Gln Glu Lys Ala His Lys
145                 150                 155                 160

Asp Leu Gln Ala Arg Cys Lys Ile Leu Ile Lys Glu Ala Asp Gln Tyr
                165                 170                 175
```

-continued

| | | | | | | | | | | | | | | | |
|---|---|---|---|---|---|---|---|---|---|---|---|---|---|---|---|
| Lys | Ala | Ala | Ala<br>180 | Asp | Asp | Val | Ser | Lys<br>185 | His | Leu | Asn | Thr | Phe<br>190 | Leu | Lys |
| Gly | Gly | Gln<br>195 | Asp | Ser | Asp | Gly | Asn<br>200 | Asp | Val | Ile | Gly | Val<br>205 | Glu | Ala | Val |
| Gln | Val<br>210 | Gln | Leu | Ala | Gln | Val<br>215 | Lys | Asp | Asn | Leu | Asp<br>220 | Gly | Leu | Tyr | Gly |
| Asp<br>225 | Lys | Ser | Pro | Arg | His<br>230 | Glu | Glu | Leu | Leu | Lys<br>235 | Lys | Val | Asp | Asp | Leu<br>240 |
| Lys | Lys | Glu | Leu | Glu<br>245 | Ala | Ala | Ile | Lys | Ala<br>250 | Glu | Asn | Glu | Leu | Glu<br>255 | Lys |
| Lys | Val | Lys | Met<br>260 | Ser | Phe | Ala | Leu | Gly<br>265 | Pro | Leu | Leu | Gly | Phe<br>270 | Val | Val |
| Tyr | Glu | Ile<br>275 | Leu | Glu | Leu | Thr | Ala<br>280 | Val | Lys | Ser | Ile | His<br>285 | Lys | Lys | Val |
| Glu | Ala<br>290 | Leu | Gln | Ala | Glu | Leu<br>295 | Asp | Thr | Ala | Asn | Asp<br>300 | Glu | Leu | Asp | Arg |
| Asp<br>305 | Val | Lys | Ile | Leu | Gly<br>310 | Met | Met | Asn | Ser | Ile<br>315 | Asp | Thr | Asp | Ile | Asp<br>320 |
| Asn | Met | Leu | Glu | Gln<br>325 | Gly | Glu | Gln | Ala | Leu<br>330 | Val | Val | Phe | Arg | Lys<br>335 | Ile |
| Ala | Gly | Ile | Trp<br>340 | Ser | Val | Ile | Ser | Leu<br>345 | Asn | Ile | Gly | Asn | Leu | Arg | Glu<br>350 |
| Thr | Ser | Leu<br>355 | Lys | Glu | Ile | Glu | Glu<br>360 | Glu | Asn | Asp | Asp | Asp<br>365 | Ala | Leu | Tyr |
| Ile | Glu<br>370 | Leu | Gly | Asp | Ala | Ala<br>375 | Gly | Gln | Trp | Lys | Glu<br>380 | Ile | Ala | Glu | Glu |
| Ala<br>385 | Gln | Ser | Phe | Val | Leu<br>390 | Asn | Ala | Tyr | Thr | Pro<br>395 | | | | | |

( 2 ) INFORMATION FOR SEQ ID NO:10:

( i ) SEQUENCE CHARACTERISTICS:
( A ) LENGTH: 22 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:10:

AGARTRK W T W AATGG W GCKM A W- 22

( 2 ) INFORMATION FOR SEQ ID NO:11:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

| | | | | | | | |
|---|---|---|---|---|---|---|---|
| Pro<br>1 | Thr | Phe | Asp | Pro<br>5 | Asp | Leu | Tyr |

( 2 ) INFORMATION FOR SEQ ID NO:12:
( i ) SEQUENCE CHARACTERISTICS:
( A ) LENGTH: 14 amino acids
( B ) TYPE: amino acid
( C ) STRANDEDNESS: single
( D ) TOPOLOGY: linear -continued ( i i ) MOLECULE TYPE: protein ( x i ) SEQUENCE DESCRIPTION: SEQ ID NO:12:

Ala Ile Leu Asn Glu Leu Tyr Pro Ser Val Pro Tyr Asn Val
1 5 10

( 2 ) INFORMATION FOR SEQ ID NO:13:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:13:

Ala Ile Leu Asn Glu Leu Tyr Pro Ser Val Pro Tyr Asn Val
1 5 10

( 2 ) INFORMATION FOR SEQ ID NO:14:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:14:

Met Ile Ile Asp Ser Lys Thr Thr Leu Pro Arg His Ser Leu Ile Asn
1 5 10 15

Thr ( 2 ) INFORMATION FOR SEQ ID NO:15:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:15:

Met Ile Leu Gly Asn Gly Lys Thr Leu Pro Lys His Ile Arg Leu Ala
1 5 10 15

His Ile Phe Ala Thr Gln Asn Ser
20

( 2 ) INFORMATION FOR SEQ ID NO:16:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:16:

GCAATTTTAA ATGAATTATA TCC 23

( 2 ) INFORMATION FOR SEQ ID NO:18:

( i ) SEQUENCE CHARACTERISTICS:
( A ) LENGTH: 38 bases
( B ) TYPE: nucleic acid
( C ) STRANDEDNESS: single -continued ( D ) TOPOLOGY: linear ( i i ) MOLECULE TYPE: DNA (synthetic)

( x i ) SEQUENCE DESCRIPTION: SEQ ID NO:18:

AAACATATTA GATTAGCACA TATTTTTGCA ACACAAAA 38

( 2 ) INFORMATION FOR SEQ ID NO:19:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:19:

CAAYTACAAG CWCAACC 17

( 2 ) INFORMATION FOR SEQ ID NO:20:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO;20:

AGGAACAAAY TCAAKWCGRT CTA 23

( 2 ) INFORMATION FOR SEQ ID NO:21:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:21:

TGGAATAAAT TCAATTYKRT CWA 23

( 2 ) INFORMATION FOR SEQ ID NO:22:

( i ) SEQUENCE CHARACTERISTICS:
( A ) LENGTH: 28 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:22:

TGATTTTWMT CAATTATATR AKGTTTAT 28

( 2 ) INFORMATION FOR SEQ ID NO:23:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:23:

AAGAGTTAYT ARARAAAGTA 20

( 2 ) INFORMATION FOR SEQ ID NO:24:

( i ) SEQUENCE CHARACTERISTICS:
( A ) LENGTH: 35 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:24:

TTAGGACCAT TRYT W GGATT TGTTGT W TAT GAAAT 35

( 2 ) INFORMATION FOR SEQ ID NO:25:

( i ) SEQUENCE CHARACTERISTICS:
( A ) LENGTH: 27 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:25:

GAYAGAGATG T W AAAATY W T AGGAATG 27

( 2 ) INFORMATION FOR SEQ ID NO:26:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:26:

TTMTTAAA W C W GCTAATGAT ATT 23

( 2 ) INFORMATION FOR SEQ ID NO:27:

( i ) SEQUENCE CHARACTERISTICS:
( A ) LENGTH: 1425 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( C ) INDIVIDUAL ISOLATE: PS86A1

( v i i ) IMMEDIATE SOURCE:
( B ) CLONE: E. coli NM522(pMYC1638) NRRL B-18751

( i x ) FEATURE:
( A ) NAME/KEY: mat peptide
( B ) LOCATION: 1..1425

( x i ) SEQUENCE DESCRIPTION: SEQ ID NO:27:

ATGATTATTG ATAGTAAAAC GACTTTACCT AGACATTCAC TTATTCATAC AATTAAATTA 60

AATTCTAATA AGAAATATGG TCCTGGTGAT ATGACTAATG GAAATCAATT TATTATTTCA 120

AAACAAGAAT GGGCTACGAT TGGAGCATAT ATTCAGACTG GATTAGGTTT ACCAGTAAAT 180

GAACAACAAT TAAGAACACA TGTTAATTTA AGTCAGGATA TATCAATACC TAGTGATTTT 240

-continued

| | | | | | | |
|---|---|---|---|---|---|---|
| TCTCAATTAT | ATGATGTTTA | TTGTTCTGAT | AAAACTTCAG | CAGAATGGTG | GAATAAAAAT | 300 |
| TTATATCCTT | TAATTATTAA | ATCTGCTAAT | GATATTGCTT | CATATGGTTT | TAAAGTTGCT | 360 |
| GGTGATCCTT | CTATTAAGAA | AGATGGATAT | TTTAAAAAAT | TGCAAGATGA | ATTAGATAAT | 420 |
| ATTGTTGATA | ATAATTCCGA | TGATGATGCA | ATAGCTAAAG | CTATTAAAGA | TTTTAAAGCG | 480 |
| CGATGTGGTA | TTTTAATTAA | AGAAGCTAAA | CAATATGAAG | AAGCTGCAAA | AAATATTGTA | 540 |
| ACATCTTTAG | ATCAATTTTT | ACATGGTGAT | CAGAAAAAAT | TAGAAGGTGT | TATCAATATT | 600 |
| CAAAAACGTT | TAAAAGAAGT | TCAAACAGCT | CTTAATCAAG | CCCATGGGGA | AAGTAGTCCA | 660 |
| GCTCATAAAG | AGTTATTAGA | AAAAGTAAAA | AATTTAAAAA | CAACATTAGA | AAGGACTATT | 720 |
| AAAGCTGAAC | AAGATTTAGA | GAAAAAAGTA | GAATATAGTT | TTCTATTAGG | ACCATTGTTA | 780 |
| GGATTTGTTG | TTTATGAAAT | TCTTGAAAAT | ACTGCTGTTC | AGCATATAAA | AAATCAAATT | 840 |
| GATGAGATAA | AGAAACAATT | AGATTCTGCT | CAGCATGATT | TGGATAGAGA | TGTTAAAATT | 900 |
| ATAGGAATGT | TAAATAGTAT | TAATACAGAT | ATTGATAATT | TATATAGTCA | AGGACAAGAA | 960 |
| GCAATTAAAG | TTTTCCAAAA | GTTACAAGGT | ATTTGGGCTA | CTATTGGAGC | TCAAATAGAA | 1020 |
| AATCTTAGAA | CAACGTCGTT | ACAAGAAGTT | CAAGATTCTG | ATGATGCTGA | TGAGATACAA | 1080 |
| ATTGAACTTG | AGGACGCTTC | TGATGCTTGG | TTAGTTGTGG | CTCAAGAAGC | TCGTGATTTT | 1140 |
| ACACTAAATG | CTTATTCAAC | TAATAGTAGA | CAAAATTTAC | CGATTAATGT | TATATCAGAT | 1200 |
| TCATGTAATT | GTTCAACAAC | AAATATGACA | TCAAATCAAT | ACAGTAATCC | AACAACAAAT | 1260 |
| ATGACATCAA | ATCAATATAT | GATTTCACAT | GAATATACAA | GTTTACCAAA | TAATTTTATG | 1320 |
| TTATCAAGAA | ATAGTAATTT | AGAATATAAA | TGTCCTGAAA | ATAATTTTAT | GATATATTGG | 1380 |
| TATAATAATT | CGGATTGGTA | TAATAATTCG | GATTGGTATA | ATAAT | | 1425 |

( 2 ) INFORMATION FOR SEQ ID NO:28:

( i ) SEQUENCE CHARACTERISTICS:
( A ) LENGTH: 475 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS86A1

( v i i ) IMMEDIATE SOURCE:
( B ) CLONE: E. coli NM522(pMYC1638) NRRL B-18751

( i x ) FEATURE:
( A ) NAME/KEY: Protein
( B ) LOCATION: 1..475

( x i ) SEQUENCE DESCRIPTION: SEQ ID NO:28:

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80
```

-continued

Ser Gln Leu Tyr Asp Val Tyr Cys Ser Asp Lys Thr Ser Ala Glu Trp
85 90 95

Trp Asn Lys Asn Leu Tyr Pro Leu Ile Ile Lys Ser Ala Asn Asp Ile
100 105 110

Ala Ser Tyr Gly Phe Lys Val Ala Gly Asp Pro Ser Ile Lys Lys Asp
115 120 125

Gly Tyr Phe Lys Lys Leu Gln Asp Glu Leu Asp Asn Ile Val Asp Asn
130 135 140

Asn Ser Asp Asp Asp Ala Ile Ala Lys Ala Ile Lys Asp Phe Lys Ala
145 150 155 160

Arg Cys Gly Ile Leu Ile Lys Glu Ala Lys Gln Tyr Glu Glu Ala Ala
165 170 175

Lys Asn Ile Val Thr Ser Leu Asp Gln Phe Leu His Gly Asp Gln Lys
180 185 190

Lys Leu Glu Gly Val Ile Asn Ile Gln Lys Arg Leu Lys Glu Val Gln
195 200 205

Thr Ala Leu Asn Gln Ala His Gly Glu Ser Ser Pro Ala His Lys Glu
210 215 220

Leu Leu Glu Lys Val Lys Asn Leu Lys Thr Thr Leu Glu Arg Thr Ile
225 230 235 240

Lys Ala Glu Gln Asp Leu Glu Lys Lys Val Glu Tyr Ser Phe Leu Leu
245 250 255

Gly Pro Leu Leu Gly Phe Val Val Tyr Glu Ile Leu Glu Asn Thr Ala
260 265 270

Val Gln His Ile Lys Asn Gln Ile Asp Glu Ile Lys Lys Gln Leu Asp
275 280 285

Ser Ala Gln His Asp Leu Asp Arg Asp Val Lys Ile Ile Gly Met Leu
290 295 300

Asn Ser Ile Asn Thr Asp Ile Asp Asn Leu Tyr Ser Gln Gly Gln Glu
305 310 315 320

Ala Ile Lys Val Phe Gln Lys Leu Gln Gly Ile Trp Ala Thr Ile Gly
325 330 335

Ala Gln Ile Glu Asn Leu Arg Thr Thr Ser Leu Gln Glu Val Gln Asp
340 345 350

Ser Asp Asp Ala Asp Glu Ile Gln Ile Glu Leu Glu Asp Ala Ser Asp
355 360 356

Ala Trp Leu Val Val Ala Gln Glu Ala Arg Asp Phe Thr Leu Asn Ala
370 375 380

Tyr Ser Thr Asn Ser Arg Gln Asn Leu Pro Ile Asn Val Ile Ser Asp
385 390 395 400

Ser Cys Asn Cys Ser Thr Thr Asn Met Thr Ser Asn Gln Tyr Ser Asn
405 410 415

Pro Thr Thr Asn Met Thr Ser Asn Gln Tyr Met Ile Ser His Glu Tyr
420 425 430

Thr Ser Leu Pro Asn Asn Phe Met Leu Ser Arg Asn Ser Asn Leu Glu
435 440 445

Tyr Lys Cys Pro Glu Asn Asn Phe Met Ile Tyr Trp Tyr Asn Asn Ser
450 455 460

Asp Trp Tyr Asn Asn Ser Asp Trp Tyr Asn Asn
465 470 475

( 2 ) INFORMATION FOR SEQ ID NO:29:

( i ) SEQUENCE CHARACTERISTICS:
( A ) LENGTH: 3471 base pairs
( B ) TYPE: nucleic acid -continued ( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: PS50C ( v i i ) IMMEDIATE SOURCE:
( B ) CLONE: E. coli NM522(pMYC2320) NRRL B-18769

( x i ) SEQUENCE DESCRIPTION: SEQ ID NO:29:

ATGAGTCCAA ATAATCAAAA TGAATATGAA ATTATAGATG CGACACCTTC TACATCTGTA 60

TCCAGTGATT CTAACAGATA CCCTTTTGCG AATGAGCCAA CAGATGCGTT ACAAAATATG 120

AATTATAAAG ATTATCTGAA AATGTCTGGG GGAGAGAATC CTGAATTATT TGGAAATCCG 180

GAGACGTTTA TTAGTTCATC CACGATTCAA ACTGGAATTG GCATTGTTGG TCGAATACTA 240

GGAGCTTTAG GGGTTCCATT TGCTAGTCAG ATAGCTAGTT TCTATAGTTT CATTGTTGGT 300

CAATTATGGC CGTCAAAGAG CGTAGATATA TGGGGAGAAA TTATGGAACG AGTGGAAGAA 360

CTCGTTGATC AAAAAATAGA AAAATATGTA AAAGATAAGG CTCTTGCTGA ATTAAAAGGG 420

CTAGGAAATG CTTTGGATGT ATATCAGCAG TCACTTGAAG ATTGGCTGGA AAATCGCAAT 480

GATGCAAGAA CTAGAAGTGT TGTTTCTAAT CAATTTATAG CTTTAGATCT TAACTTTGTT 540

AGTTCAATTC CATCTTTTGC AGTATCCGGA CACGAAGTAC TATTATTAGC AGTATATGCA 600

CAGGCTGTGA ACCTACATTT ATTGTTATTA AGAGATGCTT CTATTTTTGG AGAAGAGTGG 660

GGATTTACAC CAGGTGAAAT TTCTAGATTT TATAATCGTC AAGTGCAACT TACCGCTGAA 720

TATTCAGACT ATTGTGTAAA GTGGTATAAA ATCGGCTTAG ATAAATTGAA AGGTACCACT 780

TCTAAAAGTT GGCTGAATTA TCATCAGTTC CGTAGAGAGA TGACATTACT GGTATTAGAT 840

TTGGTGGCGT TATTTCCAAA CTATGACACA CATATGTATC CAATCGAAAC AACAGCTCAA 900

CTTACACGGG ATGTGTATAC AGATCCGATA GCATTTAACA TAGTGACAAG TACTGGATTC 960

TGCAACCCTT GGTCAACCCA CAGTGGTATT CTTTTTTATG AAGTTGAAAA CAACGTAATT 1020

CGTCCGCCAC ACTTGTTTGA TATACTCAGC TCAGTAGAAA TTAATACAAG TAGAGGGGGT 1080

ATTACGTTAA ATAATGATGC ATATATAAAC TACTGGTCAG GACATACCCT AAAATATCGT 1140

AGAACAGCTG ATTCGACCGT AACATACACA GCTAATTACG GTCGAATCAC TTCAGAAAAG 1200

AATTCATTTG CACTTGAGGA TAGGGATATT TTTGAAATTA ATTCAACTGT GGCAAACCTA 1260

GCTAATTACT ACCAAAAGGC ATATGGTGTG CCGGGATCTT GGTTCCATAT GGTAAAAAGG 1320

GGAACCTCAT CAACAACAGC GTATTTATAT TCAAAAACAC ATACAGCTCT CCAAGGGTGT 1380

ACACAGGTTT ATGAATCAAG TGATGAAATA CCTCTAGATA GAACTGTACC GGTAGCTGAA 1440

AGCTATAGTC ATAGATTATC TCATATTACC TCCCATTCTT TCTCTAAAAA TGGGAGTGCA 1500

TACTATGGGA GTTTCCCTCT ATTTGT W TGG ACACATACTA GTGCGGATTT AAATAATACA 1560

ATATATTCAG ATAAAATCAC TCAAATTCCA GCGGTAAAGG GAGACATGTT ATATCTAGGG 1620

GGTTCCGTAG TACAGGGTCC TGGATTTACA GGAGGAGATA TATTAAAAAG AACCAATCCT 1680

AGCATATTAG GGACCTTTGC GGTTACAGTA AATGGGTCGT TATCACAAAG ATATCGTGTA 1740

AGAATTCGCT ATGCCTCTAC AACAGATTTT GAATTTACTC TATACCTTGG CGACACAATA 1800

GAAAAAAATA GATTTAACAA AACTATGGAT AATGGGGCAT CTTTAACGTA TGAAACATTT 1860

AAATTCGCAA GTTTCATTAC TGATTTCCAA TTCAGAGAAA CACAAGATAA AATACTCCTA 1920

-continued

```
TCCATGGGTG ATTTTAGCTC CGGTCAAGAA GTTTATATAG ACCGAATCGA ATTCATCCCA   1980
GTAGATGAGA CATATGAGGC GGAACAAGAT TTAGAAGCGG CGAAGAAAGC AGTGAATGCC   2040
TTGTTTACGA ATACAAAAGA TGGCTTACGA CCAGGTGTAA CGGATTATGA AGTAAATCAA   2100
GCGGCAAACT TAGTGGAATG CCTATCGGAT GATTTATATC CAAATGAAAA ACGATTGTTA   2160
TTTGATGCGG TGAGAGAGGC AAAACGCCTC AGTGGGGCAC GTAACTTACT ACAAGATCCA   2220
GATTTCCAAG AGATAAACGG AGAAAATGGA TGGGCGGCAA GTACGGGAAT TGAGATTGTA   2280
GAAGGGGATG CTGTATTTAA AGGACGTTAT CTACGCCTAC CAGGTGCACG AGAAATTGAT   2340
ACGGAAACGT ATCCAACGTA TCTGTATCAA AAAGTAGAGG AAGGTGTATT AAAACCATAC   2400
ACAAGATATA GACTGAGAGG GTTTGTGGGA AGTAGTCAAG GATTAGAAAT TTATACGATA   2460
CGTCACCAAA CGAATCGAAT TGTAAAGAAT GTACCAGATG ATTTATTGCC AGATGTATCT   2520
CCTGTAAACT CTGATGGCAG TATCAATCGA TGCAGCGAAC AAAAGTATGT GAATAGCCGT   2580
TTAGAAGGAG AAAACCGTTC TGGTGATGCA CATGAGTTCT CGCTCCCTAT CGATATAGGA   2640
GAGCTGGATT ACAATGAAAA TGCAGGAATA TGGGTTGGAT TTAAGATTAC GGACCCAGAG   2700
GGATACGCAA CACTTGGAAA TCTTGAATTA GTCGAAGAGG GACCTTTGTC AGGAGACGCA   2760
TTAGAGCGCT TGCAAAGAGA AGAACAACAG TGGAAGATTC AAATGACAAG AAGACGTGAA   2820
GAGACAGATA GAAGATACAT GGCATCGAAA CAAGCGGTAG ATCGTTTATA TGCCGATTAT   2880
CAGGATCAAC AACTGAATCC TGATGTAGAG ATTACAGATC TTACTGCGGC TCAAGATCTG   2940
ATACAGTCCA TTCCTTACGT ATATAACGAA ATGTTCCCAG AAATACCAGG GATGAACTAT   3000
ACGAAGTTTA CAGAATTAAC AGATCGACTC CAACAAGCGT GGAATTTGTA TGATCAGCGA   3060
AATGCCATAC CAAATGGTGA TTTTCGAAAT GGGTTAAGTA ATTGGAATGC AACGCCTGGC   3120
GTAGAAGTAC AACAAATCAA TCATACATCT GTCCTTGTGA TTCCAAACTG GGATGAACAA   3180
GTTTCACAAC AGTTTACAGT TCAACCGAAT CAAAGATATG TATTACGAGT TACTGCAAGA   3240
AAAGAAGGGG TAGGAAATGG ATATGTAAGT ATTCGTGATG GTGGAAATCA ATCAGAAACG   3300
CTTACTTTTA GTGCAAGCGA TTATGATACA AATGGTGTGT ATAATGACCA AACCGGCTAT   3360
ATCACAAAAA CAGTGACATT CATCCCGTAT ACAGATCAAA TGTGGATTGA AATAAGTGAA   3420
ACAGAAGGTA CGTTCTATAT AGAAAGTGTA GAATTGATTG TAGACGTAGA G            3471
```

( 2 ) INFORMATION FOR SEQ ID NO:30:

( i ) SEQUENCE CHARACTERISTICS:
( A ) LENGTH: 1157 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( B ) STRAIN: kumamotoensis
( C ) INDIVIDUAL ISOLATE: PS50C ( v i i ) IMMDIATE SOURCE:
( B ) CLONE: E. coli NM522(pMYC2320) NRRL B-18769

( x i ) SEQUENCE DESCRIPTION: SEQ ID NO:30:

```
Met Ser Pro Asn Asn Gln Asn Glu Tyr Glu Ile Ile Asp Ala Thr Pro
1               5                   10                  15

Ser Thr Ser Val Ser Ser Asp Ser Asn Arg Tyr Pro Phe Ala Asn Glu
```

-continued

| | | | | | | | | | | | | | | | |
|---|---|---|---|---|---|---|---|---|---|---|---|---|---|---|---|
| | | | 20 | | | | | 25 | | | | | 30 | | |
| Pro | Thr | Asp | Ala | Leu | Gln | Asn | Met | Asn | Tyr | Lys | Asp | Tyr | Leu | Lys | Met |
| | | 3 | | | | | 40 | | | | | 45 | | | |
| Ser | Gly | Gly | Glu | Asn | Pro | Glu | Leu | Phe | Gly | Asn | Pro | Glu | Thr | Phe | Ile |
| | 50 | | | | | 55 | | | | | 60 | | | | |
| Ser | Ser | Ser | Thr | Ile | Gln | Thr | Gly | Ile | Gly | Ile | Val | Gly | Arg | Ile | Leu |
| 65 | | | | | 70 | | | | | 75 | | | | | 80 |
| Gly | Ala | Leu | Gly | Val | Pro | Phe | Ala | Ser | Gln | Ile | Ala | Ser | Phe | Tyr | Ser |
| | | | | 85 | | | | | 90 | | | | | 95 | |
| Phe | Ile | Val | Gly | Gln | Leu | Trp | Pro | Ser | Lys | Ser | Val | Asp | Ile | Trp | Gly |
| | | | 100 | | | | | 105 | | | | | 110 | | |
| Glu | Ile | Met | Glu | Arg | Val | Glu | Glu | Leu | Val | Asp | Gln | Lys | Ile | Glu | Lys |
| | | 115 | | | | | 120 | | | | | 125 | | | |
| Tyr | Val | Lys | Asp | Lys | Ala | Leu | Ala | Glu | Leu | Lys | Gly | Leu | Gly | Asn | Ala |
| | 130 | | | | | 135 | | | | | 140 | | | | |
| Leu | Asp | Val | Tyr | Gln | Gln | Ser | Leu | Glu | Asp | Trp | Leu | Glu | Asn | Arg | Asn |
| 145 | | | | | 150 | | | | | 155 | | | | | 160 |
| Asp | Ala | Arg | Thr | Arg | Ser | Val | Val | Ser | Asn | Gln | Phe | Ile | Ala | Leu | Asp |
| | | | | 165 | | | | | 170 | | | | | 175 | |
| Leu | Asn | Phe | Val | Ser | Ser | Ile | Pro | Ser | Phe | Ala | Val | Ser | Gly | His | Glu |
| | | | 180 | | | | | 185 | | | | | 190 | | |
| Val | Leu | Leu | Leu | Ala | Val | Tyr | Ala | Gln | Ala | Val | Asn | Leu | His | Leu | Leu |
| | | 195 | | | | | 200 | | | | | 205 | | | |
| Leu | Leu | Arg | Asp | Ala | Ser | Ile | Phe | Gly | Glu | Glu | Trp | Gly | Phe | Thr | Pro |
| | 210 | | | | | 215 | | | | | 220 | | | | |
| Gly | Glu | Ile | Ser | Arg | Phe | Tyr | Asn | Arg | Gln | Val | Gln | Leu | Thr | Ala | Glu |
| 225 | | | | | 230 | | | | | 235 | | | | | 240 |
| Tyr | Ser | Asp | Tyr | Cys | Val | Lys | Trp | Tyr | Lys | Ile | Gly | Leu | Asp | Lys | Leu |
| | | | | 245 | | | | | 250 | | | | | 255 | |
| Lys | Gly | Thr | Thr | Ser | Lys | Ser | Trp | Leu | Asn | Tyr | His | Gln | Phe | Arg | Arg |
| | | | 260 | | | | | 265 | | | | | 270 | | |
| Glu | Met | Thr | Leu | Leu | Val | Leu | Asp | Leu | Val | Ala | Leu | Phe | Pro | Asn | Tyr |
| | | 275 | | | | | 280 | | | | | 285 | | | |
| Asp | Thr | His | Met | Tyr | Pro | Ile | Glu | Thr | Thr | Ala | Gln | Leu | Thr | Arg | Asp |
| | 290 | | | | | 295 | | | | | 300 | | | | |
| Val | Tyr | Thr | Asp | Pro | Ile | Ala | Phe | Asn | Ile | Val | Thr | Ser | Thr | Gly | Phe |
| 305 | | | | | 310 | | | | | 315 | | | | | 320 |
| Cys | Asn | Pro | Trp | Ser | Thr | His | Ser | Gly | Ile | Leu | Phe | Tyr | Glu | Val | Glu |
| | | | | 325 | | | | | 330 | | | | | 335 | |
| Asn | Asn | Val | Ile | Arg | Pro | Pro | His | Leu | Phe | Asp | Ile | Leu | Ser | Ser | Val |
| | | | 340 | | | | | 345 | | | | | 350 | | |
| Glu | Ile | Asn | Thr | Ser | Arg | Gly | Gly | Ile | Thr | Leu | Asn | Asn | Asp | Ala | Tyr |
| | | 355 | | | | | 360 | | | | | 365 | | | |
| Ile | Asn | Tyr | Trp | Ser | Gly | His | Thr | Leu | Lys | Tyr | Arg | Arg | Thr | Ala | Asp |
| | 370 | | | | | 375 | | | | | 380 | | | | |
| Ser | Thr | Val | Thr | Tyr | Thr | Ala | Asn | Tyr | Gly | Arg | Ile | Thr | Ser | Glu | Lys |
| 385 | | | | | 390 | | | | | 395 | | | | | 400 |
| Asn | Ser | Phe | Ala | Leu | Glu | Asp | Arg | Asp | Ile | Phe | Glu | Ile | Asn | Ser | Thr |
| | | | | 405 | | | | | 410 | | | | | 415 | |
| Val | Ala | Asn | Leu | Ala | Asn | Tyr | Tyr | Gln | Lys | Ala | Tyr | Gly | Val | Pro | Gly |
| | | | 420 | | | | | 425 | | | | | 430 | | |
| Ser | Trp | Phe | His | Met | Val | Lys | Arg | Gly | Thr | Ser | Ser | Thr | Thr | Ala | Tyr |
| | | 435 | | | | | 440 | | | | | 445 | | | |
| Leu | Tyr | Ser | Lys | Thr | His | Thr | Ala | Leu | Gln | Gly | Cys | Thr | Gln | Val | Tyr |
| | 450 | | | | | 455 | | | | | 460 | | | | |

-continued

```
Glu Ser Ser Asp Glu Ile Pro Leu Asp Arg Thr Val Pro Val Ala Glu
465                 470                 475                 480

Ser Tyr Ser His Arg Leu Ser His Ile Thr Ser His Ser Phe Ser Lys
                485                 490                 495

Asn Gly Ser Ala Tyr Tyr Gly Ser Phe Pro Val Phe Val Trp Thr His
            500                 505                 510

Thr Ser Ala Asp Leu Asn Asn Thr Ile Tyr Ser Asp Lys Ile Thr Gln
        515                 520                 525

Ile Pro Ala Val Lys Gly Asp Met Leu Tyr Leu Gly Gly Ser Val Val
    530                 535                 540

Gln Gly Pro Gly Phe Thr Gly Gly Asp Ile Leu Lys Arg Thr Asn Pro
545                 550                 555                 560

Ser Ile Leu Gly Thr Phe Ala Val Thr Val Asn Gly Ser Leu Ser Gln
                565                 570                 575

Arg Tyr Arg Val Arg Ile Arg Tyr Ala Ser Thr Thr Asp Phe Glu Phe
            580                 585                 590

Thr Leu Tyr Leu Gly Asp Thr Ile Glu Lys Asn Arg Phe Asn Lys Thr
        595                 600                 605

Met Asp Asn Gly Ala Ser Leu Thr Tyr Glu Thr Phe Lys Phe Ala Ser
    610                 615                 620

Phe Ile Thr Asp Phe Gln Phe Arg Glu Thr Gln Asp Lys Ile Leu Leu
625                 630                 635                 640

Ser Met Gly Asp Phe Ser Ser Gly Gln Glu Val Tyr Ile Asp Arg Ile
                645                 650                 655

Glu Phe Ile Pro Val Asp Glu Thr Tyr Glu Ala Glu Gln Asp Leu Glu
            660                 665                 670

Ala Ala Lys Lys Ala Val Asn Ala Leu Phe Thr Asn Thr Lys Asp Gly
        675                 680                 685

Leu Arg Pro Gly Val Thr Asp Tyr Glu Val Asn Gln Ala Ala Asn Leu
    690                 695                 700

Val Glu Cys Leu Ser Asp Asp Leu Tyr Pro Asn Glu Lys Arg Leu Leu
705                 710                 715                 720

Phe Asp Ala Val Arg Glu Ala Lys Arg Leu Ser Gly Ala Arg Asn Leu
                725                 730                 735

Leu Gln Asp Pro Asp Phe Gln Glu Ile Asn Gly Glu Asn Gyl Trp Ala
            740                 745                 750

Ala Ser Thr Gly Ile Glu Ile Val Glu Gly Asp Ala Val Phe Lys Gly
        755                 760                 765

Arg Tyr Leu Arg Leu Pro Gly Ala Arg Glu Ile Asp Thr Glu Thr Tyr
    770                 775                 780

Pro Thr Tyr Leu Tyr Gln Lys Val Glu Glu Gly Val Leu Lys Pro Tyr
785                 790                 795                 800

Thr Arg Tyr Arg Leu Arg Gly Phe Val Gly Ser Ser Gln Gly Leu Glu
                805                 810                 815

Ile Tyr Thr Ile Arg His Gln Thr Asn Arg Ile Val Lys Asn Val Pro
            820                 825                 830

Asp Asp Leu Leu Pro Asp Val Ser Pro Val Asn Ser Asp Gly Ser Ile
        835                 840                 845

Asn Arg Cys Ser Glu Gln Lys Tyr Val Asn Ser Arg Leu Glu Gly Glu
    850                 855                 860

Asn Arg Ser Gly Asp Ala His Glu Phe Ser Leu Pro Ile Asp Ile Gly
865                 870                 875                 880

Glu Leu Asp Tyr Asn Glu Asn Ala Gly Ile Trp Val Gly Phe Lys Ile
                885                 890                 895
```

-continued

| | | | | | | | | | | | | | | | |
|---|---|---|---|---|---|---|---|---|---|---|---|---|---|---|---|
| Thr | Asp | Pro | Glu | Gly | Tyr | Ala | Thr | Leu | Gly | Asn | Leu | Glu | Leu | Val | Glu |
| | | | 900 | | | | | 905 | | | | | 910 | | |
| Glu | Gly | Pro | Leu | Ser | Gly | Asp | Ala | Leu | Glu | Arg | Leu | Gln | Arg | Glu | Glu |
| | | 915 | | | | | 920 | | | | | 925 | | | |
| Gln | Gln | Trp | Lys | Ile | Gln | Met | Thr | Arg | Arg | Arg | Glu | Glu | Thr | Asp | Arg |
| | 930 | | | | | 935 | | | | | 940 | | | | |
| Arg | Tyr | Met | Ala | Ser | Lys | Gln | Ala | Val | Asp | Arg | Leu | Tyr | Ala | Asp | Tyr |
| 945 | | | | | 950 | | | | | 955 | | | | | 960 |
| Gln | Asp | Gln | Gln | Leu | Asn | Pro | Asp | Val | Glu | Ile | Thr | Asp | Leu | Thr | Ala |
| | | | | 965 | | | | | 970 | | | | | 975 | |
| Ala | Gln | Asp | Leu | Ile | Gln | Ser | Ile | Pro | Tyr | Val | Tyr | Asn | Glu | Met | Phe |
| | | | 980 | | | | | 985 | | | | | 990 | | |
| Pro | Glu | Ile | Pro | Gly | Met | Asn | Tyr | Thr | Lys | Phe | Thr | Glu | Leu | Thr | Asp |
| | | 995 | | | | | 1000 | | | | | 1005 | | | |
| Arg | Leu | Gln | Gln | Ala | Trp | Asn | Leu | Tyr | Asp | Gln | Arg | Asn | Ala | Ile | Pro |
| | 1010 | | | | | 1015 | | | | | 1020 | | | | |
| Asn | Gly | Asp | Phe | Arg | Asn | Gly | Leu | Ser | Asn | Trp | Asn | Ala | Thr | Pro | Gly |
| 1025 | | | | | 1030 | | | | | 1035 | | | | | 1040 |
| Val | Glu | Val | Gln | Gln | Ile | Asn | His | Thr | Ser | Val | Leu | Val | Ile | Pro | Asn |
| | | | | 1045 | | | | | 1050 | | | | | 1055 | |
| Trp | Asp | Glu | Gln | Val | Ser | Gln | Gln | Phe | Thr | Val | Gln | Pro | Asn | Gln | Arg |
| | | | 1060 | | | | | 1065 | | | | | 1070 | | |
| Tyr | Val | Leu | Arg | Val | Thr | Ala | Arg | Lys | Glu | Gly | Val | Gly | Asn | Gly | Tyr |
| | | 1075 | | | | | 1080 | | | | | 1085 | | | |
| Val | Ser | Ile | Arg | Asp | Gly | Gly | Asn | Gln | Ser | Glu | Thr | Leu | Thr | Phe | Ser |
| | 1090 | | | | | 1095 | | | | | 1100 | | | | |
| Ala | Ser | Asp | Tyr | Asp | Thr | Asn | Gly | Val | Tyr | Asn | Asp | Gln | Thr | Gly | Tyr |
| 1105 | | | | | 1110 | | | | | 1115 | | | | | 1120 |
| Ile | Thr | Lys | Thr | Val | Thr | Phe | Ile | Pro | Tyr | Thr | Asp | Gln | Met | Trp | Ile |
| | | | | 1125 | | | | | 1130 | | | | | 1135 | |
| Glu | Ile | Ser | Glu | Thr | Glu | Gly | Thr | Phe | Tyr | Ile | Glu | Ser | Val | Glu | Leu |
| | | | 1140 | | | | | 1145 | | | | | 1150 | | |
| Ile | Val | Asp | Val | Glu | | | | | | | | | | | |
| | | 1155 | | | | | | | | | | | | | |

*BACILLUS THURINGIENSIS* ISOLATES FOR CONTROLLING ACARIDES

CROSS-REFERENCE TO A RELATED APPLICATION

This is a division, of application Ser. No. 07/867,280 filed Apr. 30, 1992, now U.S. Pat. No. 5,262,158, which is a continuation-in-part of application Ser. No. 07/693,210, filed on Apr. 30, 1991 now abandoned. This is also a continuation-in-part of application Ser. No. 07/768,141, filed on Sep. 30, 1991 now U.S. Pat. No. 5,211,946, which is a continuation-in-part of application Ser. No. 07/759,248, filed on Sep. 13, 1991, now abandoned.

BACKGROUND OF THE INVENTION

The spore-forming microorganism *Bacillus thuringiensis* (B.t.) produces the best-known insect toxin. The toxin is a protein, designated as δ-endotoxin. It is synthesized by the B.t. sporulating cell. The toxin, upon being ingested in its crystalline form by susceptible insect larvae, is transformed into biologically active moieties by the insect gut juice proteases. The primary target is insect cells of the gut epithelium, which are rapidly destroyed. Experience has shown that the activity of the B.t. toxin is so high that only nanogram amounts are required to kill susceptible insects.

The reported activity spectrum of B.t. covers insect species within the order Lepidoptera, which is a major insect problem in agriculture and forestry. The activity spectrum also includes the insect order Diptera, wherein reside mosquitoes and blackflies. See Couch, T. L., (1980) "Mosquito Pathogenicity of *Bacillus thuringiensis* var. *israelensis*," Developments in Industrial Microbiology, 22:61-67; Beegle, C. C., (1978) "Use of Entomogeneous Bacteria in Agroecosystems," Developments in Industrial Microbiology, 20:97-104.

U.S. Pat. No. 4,771,131 discloses a toxin gene isolated from a strain of *Bacillus thuringiensis*. This gene encodes a toxin which is active against beetles of the order Coleoptera.

There have been published reports concerning the use of *Bacillus thuringiensis* preparations for the control of mites. These publications are as follow:

Royalty, R. N., HaH, F. R. and Taylor, R. A. J. 1990. Effects of *thuringiensin* on *Tetranychus urticae* (Acari: Tetranychidae) mortality, fecundity, and feeding. J. Econ. Entomol. 83:792-798.

Neal, J. W., Lindquist, R. K., Gott, K. M. and Casey, M. L. 1987. Activity of the themostable beta-exotoxin of *Bacillus thuringiensis* Berliner on *Tetranychus urticae* and *Tetranychus cinnabarinus*. J. Agric. Entomol. 4:33-40.

Vlayen, P., Impe, G. and Van Semaille, R. 1978. Effect of a commercial preparation of *Bacillus thuringiensis* on the spider mite *Tetranychus urticae* Koch. (Acari: Tetranychidae). Mededelingen 43:471-479.

In the above published studies, the active ingredient in the B.t. preparations was beta-exotoxin (also called *thuringiensin*).

U.S. Pat. No. 4,695,455 concerns methods and compositions for preparing and using biological pesticides, where the pesticides are encapsulated in non-proliferating cells.

U.S. Pat. No. 4,849,217 concerns B.t. isolates active against the alfalfa weevil.

BRIEF SUMMARY OF THE INVENTION

The subject invention concerns *Bacillus thuringiensis* isolates and toxins which have acaricidal properties. Unlike published reports of the use of B.t. β-exotoxins to control mites, the subject invention isolates express δ-endotoxins which control mites. The use of δ-endotoxins is highly advantageous in view of the known general toxicity of δ-exotoxins to humans and animals.

More specifically, the subject invention concerns *Bacillus thuringiensis* isolates designated B.t. PS50C, B.t. PS86A1, B.t. PS69D1, B.t. PS72L1, B.t. PS75J1, B.t. PS83E5, B.t. PS45B1, B.t. PS24J, B.t. PS94R3, B.t. PS17, B.t. PS62B1 and B.t. PS74G1.

The B.t. isolates of the subject invention are toxic to the Two Spotted Spider Mite, *Tetranychus urticae*. Thus, these isolates can be used to control this mite. Further, the δ-endotoxins from these B.t. isolates can be isolated by standard procedures, e.g. ion exchange, and formulated by standard procedures to control the Two Spotted Spider Mite. These B.t. isolates can also be used against non-phytophagus mites such as acarid pests of livestock, fowl and stored products. Still further, the gene(s) from the B.t. isolates of the invention which encode the acaricidal toxin can be cloned from the isolates and then used to transform other hosts, e.g., prokaryotic, eukaryotic or plants, which transformed host can be used to control mites, or, in the case of transgenic plants, be resistant to mites.

BRIEF DESCRIPTION OF THE SEQUENCES

Figure 1:
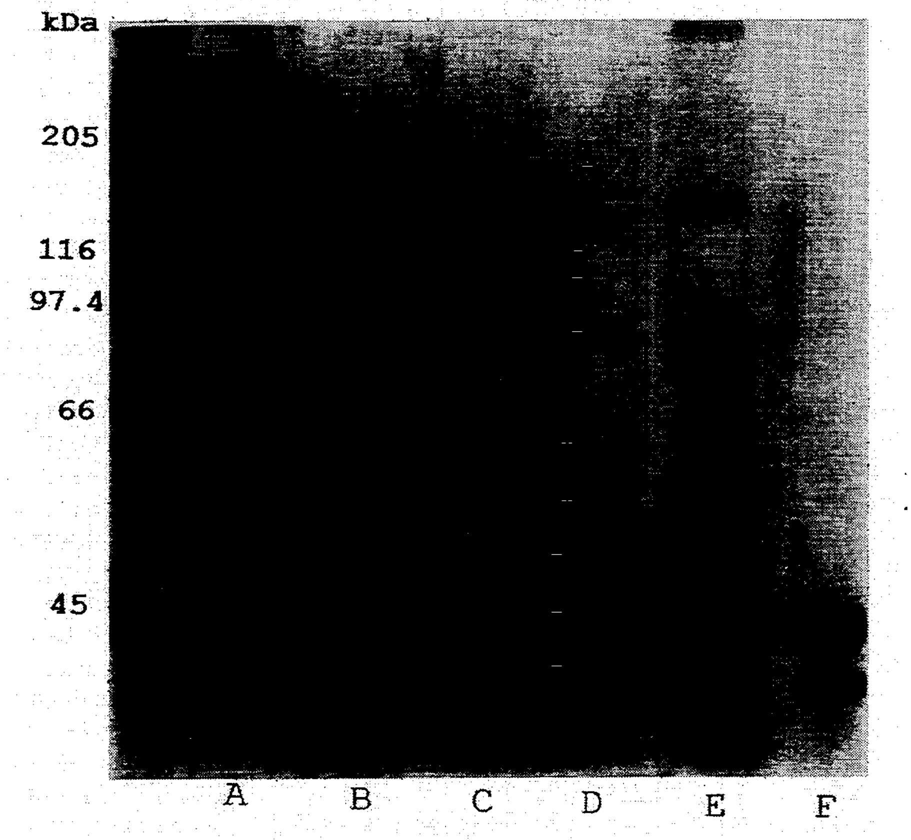
FIGS. 1, 2A and 2B are photographs of 12% SDS polyacrylamide gels showing alkali-soluble proteins of the isolates of the invention.
Figure 2A:
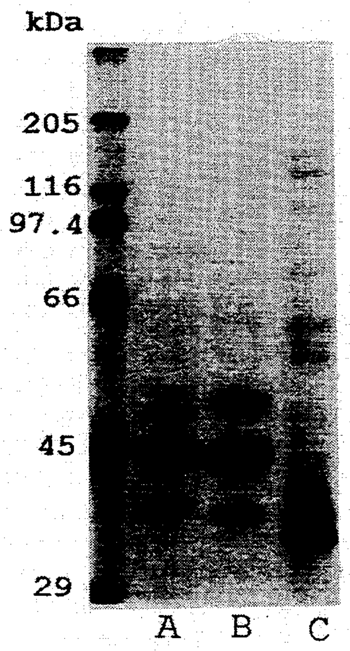
Figure 2B:
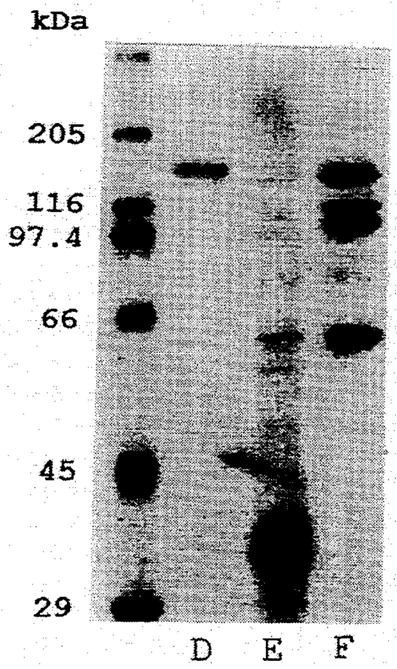

SEQ ID NO. 1 discloses the DNA of 17a.

SEQ ID NO. 2 discloses the amino acid sequence of the toxin encoded by 17a.

SEQ ID NO. 3 discloses the DNA of 17b.

SEQ ID NO. 4 discloses the amino acid sequence of the toxin encoded by 17b.

SEQ ID NO. 5 is the nucleotide sequence of gene 33F2.

SEQ ID NO. 6 is the nucleotide sequence of a gene from 52A1.

SEQ ID NO. 7 is the amino acid sequence of the protein expressed by the gene from 52A1.

SEQ ID NO. 8 is the nucleotide sequence of a gene from 69D1.

SEQ ID NO. 9 is the amino acid sequence of the protein expressed by the gene from 69D1.

SEQ ID NO. 10 is the DNA coding for the amino acid sequence of SEQ ID NO. 13.

SEQ ID NO. 11 is the amino acid sequence of a probe which can be used according to the subject invention.

SEQ ID NO. 12 is the N-terminal amino acid sequence of 17a.

SEQ ID NO. 13 is the N-terminal amino acid sequence of 17b.

SEQ ID NO. 14 is the N-terminal amino acid sequence of 52A1.

SEQ ID NO. 15 is the N-terminal amino acid sequence of 69D1.

SEQ ID NO. 16 is a synthetic oligonucleotide derived from 17.

SEQ ID NO. 17 is an oligonucleotide probe designed from the N-terminal amino acid sequence of 52A1.

SEQ ID NO. 18 is the synthetic oligonucleotide probe designated as 69D1D.

SEQ ID NO. 19 is the forward oligonucleotide primer from 63B.

SEQ ID NO. 20 is the reverse complement primer to SEQ ID NO. 29, used according to the subject invention.

SEQ ID NO. 21 is the DNA coding for the primer of SEQ ID NO. 31.

SEQ ID NO. 22 is a forward primer according to the subject invention.

SEQ ID NO. 23 is a probe according to the subject invention.

SEQ ID NO. 24 is a probe according to the subject invention.

SEQ ID NO. 25 is a probe according to the subject invention.

SEQ ID NO. 26 is a forward primer according to the subject invention.

SEQ ID NO. 27 is the nucleotide sequence of a gene from PS50C.

SEQ ID NO. 28 is the amino acid sequence of the protein expressed by the gene from PS50C.

SEQ ID NO. 29 is the nucleotide sequence of a gene from PS86A1.

SEQ ID NO. 30 is the amino acid sequence of the protein expressed by the gene from PS86A1.

DETAILED DISCLOSURE OF THE INVENTION

The subject invention concerns B.t. δ-endotoxins having acaricidal activity. In addition to having acaricidal activity, the toxins of the subject invention may have one or more of the following characteristics:

1. A high degree of amino acid homology with specific toxins disclosed herein.
2. A DNA sequence encoding the toxin which hybridizes with probes or genes disclosed herein.
3. A nucleotide sequence which can be amplified using primers disclosed herein.
4. Immunoreactivity to an antibody raised to a specific toxin disclosed herein.

Acaride-active toxins according to the subject invention are specifically exemplified herein by the toxins encoded by the genes designated 17a, 17b, and 69D 1. Since these toxins are merely exemplary of the toxins presented herein, it should be readily apparent that the subject invention further comprises toxins from the other disclosed isolates as well as equivalent toxins (and nucleotide sequences coding for equivalent toms) having the same or similar biological activity of the specific toxins disclosed or claimed herein. These equivalent toxins will have amino acid homology with the toxins disclosed and claimed herein. This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. The information presented in the generic formulae of the subject invention provides clear guidance to the person skilled in this art in making various amino acid substitutions.

The B.t. isolates of the invention have the following characteristics:

| Strain | Crystal Type | Approx. Mol. Wt. of Proteins (kDa) B. |
|---|---|---|
| *thuringiensis* PS50C | Sphere | 135 doublet |
| *B. thuringiensis* PS86A1 | Multiple | 45, 58 |
| *B. thuringiensis* PS69D1 | Elongated | 34, 48, 145 |
| *B. thuringiensis* PS72L1 | Long rectangle | 42, 50 |
| *B. thuringiensis* PS75J1 | Amorphic | 63, 74, 78, 84 |
| *B. thuringiensis* PS83E5 | Multiple | 37, 42 |
| *B. thuringiensis* PS24J | Long | 51, 48, 43 |
| *B. thuringiensis* PS94R3 | Long | 50, 43, 42 |
| *B. thuringiensis* PS45B1 | Multiple | 150, 135, 35 |
| *B. thuringiensis* PS17 | Long | 155, 145, 128 |
| *B. thuringiensis* PS62B1 | Attached multiple | 35 |
| *B. thuringiensis* PS74G1 | Amorphic | 148, 112, 104, 61 |

Additionally, the isolates have the following common characteristics:

Colony morphology—large colony, dull surface, typical B.t.

Vegetative cell morphology—typical B.t.

The toxins of the subject invention can be accurately characterized in terms of the shape and location of crystal toxin inclusions. Specifically, acaride-active inclusions typically remain attached to the spore after cell lysis. These inclusions are not inside the exosporium, as in previous descriptions of attached inclusions, but are held within the spore by another mechanism. Inclusions of the acaride-active isolates are typically amorphie, generally long and/or multiple. These inclusions are distinguishable from the larger round-/amorphic inclusions that remain attached to the spore. No B.t. strains that fit this description have been found to have activity against the conventional targets—Lepidoptera, Diptera, or Colorado Potato Beetle. We have found a very high correlation between this crystal structure and acaride activity.

The genes and toxins according to the subject invention include not only the full length sequences disclosed herein but also fragments of these sequences, or fusion proteins, which retain the characteristic acaricidal activity of the sequences specifically exemplified herein.

It should be apparent to a person skilled in this art that genes coding for acaride-active toxins can be identified and obtained through several means. The specific genes may be obtained from a culture depository as described below. These genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Ba131 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be located from B.t. isolates and/or DNA libraries using the teachings provided herein. There are a number of methods for obtaining the acaride-active toxins of the instant invention which occur in nature. For example, antibodies to the acaride-active toxins disclosed and claimed herein can be used to identify and isolate other toxins from a mixture of proteins. Specifically, antibodies may be raised to the acaride-active toxins using procedures which are well known in the art. These antibodies can then be used to specifically identify equivalent toxins with the characteristic acaricidal activity by immunoprecipitation, enzyme linked immunoassay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying nematicidal endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}$p, $^{125}$i, $^{35}$S, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perixodases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed test sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful, according to the subject invention, in the rapid identification of acaride-active genes can be prepared utilizing the sequence information provided herein.

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the B.t. toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

The B.t. isolates of the invention, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains. The novel B.t. isolates, and mutants thereof, can be used to control target pests.

The cultures of the subject invention were deposited in the Agricultural Research Service Patent Culture Collection (NRRL), Northern Regional Research Center, 1815 North University Street, Peoria, Ill., 61604 USA.

| Culture | Accession No. | Deposit Date |
|---|---|---|
| *B.t.* PS50C | NRRL B-18746 | January 9, 1991 |
| *B.t.* PS86A1 | NRRL B-18400 | August 16, 1988 |
| *B.t.* PS69D1 | NRRL B-18247 | July 28, 1987 |
| *B.t.* PS72L1 | NRRL B-18780 | March 7, 1991 |
| *B.t.* PS75J1 | NRRL B-18781 | March 7, 1991 |
| *B.t.* PS83E5 | NRRL B-18782 | March 7, 1991 |
| *B.t.* PS45B1 | NRRL B-18396 | August 16, 1988 |
| *B.t.* PS24J | NRRL B-18881 | August 30, 1991 |
| *B.t.* PS94R3 | NRRL B-18882 | August 30, 1991 |
| *B.t.* PS17 | NRRL B-18243 | July 28, 1987 |
| *B.t.* PS62B1 | NRRL B-18398 | August 16, 1988 |
| *B.t.* PS74G1 | NRRL B-18397 | August 16, 1988 |
| *E. coli* NM522(pNffC 2321) | NRRL B-18770 | February 14, 1991 |
| *E. coli* NM522(pMYC 2317) | NRRL B-18816 | April 24, 1991 |
| *E. coli* NM522(pNffC 1627) | NRRL B-18651 | May 11, 1990 |
| *E. coli* NM522(pMYC 1628) | NRRL B-18652 | May 11, 1990 |
| *E. coli* NM522(pMYC 1638) | NRRL B-18751 | January 11, 1991 |
| *E. coli* NM522(pMYC 1638) | NRRL B-18769 | February 14, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

Upon applying an acaricidal-effective amount of a microbe, or toxin, as disclosed herein, in a suitable acaricidal formulation to the environment of the target pest, there is obtained effective control of these pests. An ataritidal-effective amount can vary from about 1 to about 12 l/ha, depending upon the nature and quantity of the pests to be controlled, the time of year, temperature, humidity, and other known factors which may affect a bioinsecticide. It is well within the skill of those trained in this an to determine the quantity of bioinsecticide to apply in order to obtain effective control of target pests.

The intracellular δ-endotoxin protein can be combined with other insecticidal proteins (including those obtained from sources other than *Bacillus thuringiens*) to increase the spectrum of activity to give complete control of target pests.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95 % by weight of the pesticide while the liquid formulations will generally be from about 1–60% by weight of the solids in the liquid phase. The formulations will generally have from about 102 to about $10^4$ cells/mg. These formulations will be administered at about 50 mg (liquid or dry) to 1 kg or more per hectare.

The formulations can be applied to the environment of the target pest(s), e.g., plants, livestock, fowl, soil or water, by spraying, dusting, sprinkling, or the like.

The toxin genes harbored by the novel isolates of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of mites where they will proliferate and be ingested by the mites. The result is a control of the mites. Alternatively, the microbe hosting the toxin gene can be treated under conditions that prolong the activity of the toxin produced in the cell. The treated cell then can be applied to the environment of the target pest. The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots). These microorganisms include bacteria, algae, and fungi. Of particular interest are microorganisms, such as bacteria, e.g., genera Bacillus, Pseudomonas, Erwinia, Serratia, Klebsiella Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes and Clostridium; fungi, particularly yeast, e.g., genera Saccharomyces, Cryptococcus, Kluyveromyces, Sporobolomyces, Rhodotorula, and Aureobasidium; microalgae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustimanatophyceae, Cryptophyceae, Euglenophyceae, Prasinophyceae, and Chlorophyceae. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrohphus,* and *Azotobacter vinlandii;* and phytosphere yeast species such as *Rhodotorula rubra, R. glutinis, R. marina, R. aurantiaca, Cryptococcus albidus, C. diffiuens, C. laurentii, Saccharomyces rosei, S. pretoriensis, S. cerevisiae, Sporobolomyces roseus, S. odorus, Kluyverornyces veronae,* and *Aureobasidium pollulans.* Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a to xin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 5000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi, as disclosed previously.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t, spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulated bait granules containing an attractant and spores and crystals of the B.t. isolates, or recombinant microbes comprising the gene(s) obtainable from the B.t. isolates disclosed herein, can be applied to the soil or in the vicinity of stored products. Formulated product can also be applied as a seed-coating or root treatment or total plant treatment at later stages of the crop cycle.

Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those routants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing of the B.t. Isolates

A subculture of the B.t. isolates, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | 3.66 g |
| $CaCl_2.2H_2O$ | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Purification of Protein and Amino Acid Sequencing

The B.t. isolates PS17, PS52A1 and PS69D1 were cultured as described in Example 1. The parasporal inclusion bodies were partially purified by sodium bromide (28–38%) isopycnic gradient centrifugation (Pfannenstiel, M. A., E. J. Ross, V. C. Kramer, and K. W. Nickerson [1984] FEMS Microbiol. Lett. 21:39). The proteins were bound to PVDF membranes (Millipore, Bedford, Mass.) by western blotting techniques (Towbin, H., T. Staehlelin, and K. Gordon [1979] Proc. Natl. Acad. Sci. USA 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] Meth. Enzymol. 91:399). The sequences obtained were:

PS17a: A I L N E L Y P S V P Y N V (SEQ ID NO. 12)

PS17b: A I L N E L Y P S V P Y N V (SEQ ID NO. 13)

PS52A1: M I I D S K T T L P R H S L I N T (SEQ ID NO. 14)

PS69D1: M I L G N G K T L P K H I R L A H I F A T Q N S (SEQ ID NO. 15)

EXAMPLE 3

Cloning of Novel Toxin Genes and Transformation into *Escherichia coli*

Total cellular DNA was prepared by growing the cells B.t. PS17 to a low optical density ($OD_{600}$=1.0) and recovering the cells by centrifugation. The cells were protoplasted in TES buffer (30 mM Tris-Cl, 10 mM EDTA, 50 mM NaCl, pH =8.0) containing 20 % sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCl, 20 mM NaOAc, 2.5 mM EDTA, pH=8.0) buffered gel. A Southern blot of the gel was hybridized with a [$^{32}$p]—radiolabeled oligonucleotide probe derived from the N-terminal amino acid sequence of purified 130 kDa protein from PS17. The sequence of the oligonucleotide synthesized is (GCAATITFAAATGAATrATATCC) (SEQ ID NO. 16). Results showed that the hybridizing EcoRI fragments of PS17 are 5.0 kb, 4.5 kb, 2.7 kb and 1.8 kb in size, presumptively identifying at least four new acaride-active toxin genes, PS17d, PS17b, PS17a and PS17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip TM ion exchange column (Schleicher and Schuel, Keene N.H.). The isolated Sau3A fragments were ligated into LambdaGEM-11 TM (PROMEGA). The packaged phage were plated on KW25 1 *E. coli* cells (PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 *E. coli* cells in liquid culture for preparation of phage for DNA isolation. DNA was isolated by standard procedures.

Recovered recombinant phage DNA was digested with EcoRI and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (PS17b) or the 2.7 kb (PS17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pBClac, an *E. coli*/B.t. shuttle vector comprised of replication origins from pBC16 and pUC19. The ligation mix was introduced by transformation into NM522 competent *E. coli* cells and plated on LB agar containing ampicillin, isopropyl-(Beta)-D-thiogalactoside(IPTG) and S-Bromo-4-Chloro- 3-indolyl-(Beta)-D-galactoside (XGAL). White colonies, with putative insertions in the (Beta)galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The PS17 toxin genes were subcloned into the shuttle vector pHT3101 (Lereclus, D. et al. [1989] FEMS Microbiol. Lett. 60:211–218) using standard methods for expression in B.t. Briefly, SalI fragments containing the 17a and 17b toxin genes were isolated from pMYC1629 and pMYC1627, respectively, by preparative agarose gel electrophoresis, electroelution, and concentrated, as described above. These concentrated fragments were ligated into SalI-cleaved and dephosphorylated pHT3101. The ligation mixtures were used separately to transform frozen, competent *E. coli* NM522. Plasmids from each respective recombinant *E. coli* strain were prepared by alkaline lysis and analyzed by agarose gel electrophoresis. The resulting subclones, pMYC2311 and pMYC2309, harbored the 17a and 17b toxin genes, respectively. These plasmids were transformed into the acrystalliferous B.t. strain, HD-1 cryB (Aronson, A., Purdue University, West Lafayette, Ind.), by standard electroporation techniques (Instruction Manual, Biorad, Richmond, Calif.).

Recombinant B.t. strains HD-1 cryB [pMYC2311] and [pMYC2309] were grown to sporulation and the proteins purified by NaBr gradient centrifugation as described above for the wild-type B.t. proteins.

EXAMPLE 4

Molecular Cloning of Gene Encoding a Novel Toxin From *Bacillus thuringiensis* strain PS52A1

Total cellular DNA was prepared from *Bacillus thuringiensis* PS52A1 (B.t. PS52A1) as disclosed in Example 3.

RFLP analyses were performed by standard hybridization of Southern blots of PS52A1 DNA with a $^{32}P$-labeled oligonucleotide probe designed from the N-terminal amino acid sequence disclosed in Example 2. The sequence of this probe is:

5' ATG ATT ATT GAT TCT AAA ACA ACA TTA CCA AGA CAT TCA/T TTA ATA/T AAT ACA/T ATA/T AA 3' (SEQ ID NO. 17)

This probe was designated 52A1-C. Hybridizing bands included an approximately 3.6 kbp HindIII fragment and an approximately 8.6 kbp EcoRV fragment. A gene library was constructed from PS52A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BarnHI-digested LambdaGem-11 (Promega). Recombinant phage were packaged and plated on *E. coli* KW251 cells (Promega). Plaques were screened by hybridization with the radiolabeled 52A1-C oligonucleotide probe disclosed above. Hybridizing phage were plaque-purified and used to infect liquid cultures of *E. coli* KW251 cells for isolation of phage DNA by standard procedures (Maniatis et al.). For subcloning, preparative amounts of DNA were digested with EcoRI and SalI, and electrophoresed on an agarose gel. The approximately 3.1 kbp band containing the toxin gene was excised from the gel, electroeluted from the gel slice, and purified by ion exchange chromatography as above. The purified DNA insert was ligated into EcoRI +SalI-digested pHTBlueII (an *E. coli/B. thuringiensis* shuttle vector comprised of pBluescript S/K [Stratagene] and the replication origin from a resident B.t. plasmid [D. Lereclus et al. 1989. FEMS Microbiology Letters 60:211–218]). The ligation mix was used to transform frozen, competent *E. coli* NM522 cells (ATCC 47000). Transformants were plated on LB agar containing ampicillin, isopropyl-(Beta)-D-thiogalactoside (IPTG), and 5-Bromo-4-Chloro-3-indolyl-(Beta)-D-galactoside (XGAL). Plasmids were purified from putalive recombinants by alkaline lysis (Manialls et al.) and analyzed by electrophoresis of EcoRI and SalI digests on agarose gels. The desired plasmid construct, pMYC2321 contains a toxin gene that is novel compared to the maps of other toxin genes encoding acaricidal proteins.

Plasmid pMYC2321 was introducèd into an acrystalliferous (Cry−) B.t. host by electropotation. Expression of an approximately 55–60 kDa crystal protein was verified by SDS-PAGE analysis.

EXAMPLE 5

Molecular Cloning of Gene Encoding a Novel Toxin From *Bacillus Thuringiensis* strain PS69D1

Total cellular DNA was prepared from PS69D1 (B.t. PS69D1) as disclosed in Example 3. RFLP analyses were performed by standard hybridization of Southern blots of PS69D1 DNA with a 32P-labeled oligonucleotide probe designated as 69D1D. The sequence of the 69D1-D probe was:

5' AAA CAT ATT AGA TTA GCA CAT ATT TTT GCA ACA CAA AA 3' (SEQ ID NO. 18)

Hybridizing bands included an approximately 2.0 kbp HindIII fragment.

A gene library was constructed from PS69D1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega, Madison, Wis.). Recombinant phage were packaged and plated on *E. coli* KW251 cells (Promega, Madison, Wis.). Plaques were screened by hybridization with the radiolabeled 69D1-D oligonucleotide probe. Hybridizing phage were plaque-purified and used to infect liquid cultures of *E. coli* KW251 cells for isolation of phage DNA by standard procedures (Maniatis et al. [1982] *Molecular Cloning: A Laboratory Manual,* Cold Spring Harbor, N.Y.). For subcloning, preparative amounts of DNA were digested with HindIII and electrophoresed on an agarose gel. The approximately, 2.0 kbp band containing the toxin gene was excised from the gel, electroeluted from the gel slice, and purified by ion exchange chromatography as above. The purified DNA insert was ligated into HindlII-digested pHTBluell (and *E. coli*/B.t. shuttle vector comprised of pBluescript S/K (Stratagene, San Diego, Calif.) and the replication origin from a resident B.t. plasmid (D. Lereclus et al [1989] FEMS Microbiol. Lett. 60:211-218). The ligation mix was used to transform frozen, competent *E. coli* NM522 cells (ATCC 47000). Transformants were plated on LB agar containing 5-bromo-4-chloro-3-indolyl-(Beta)-D-galactoside (XGAL). Plasmids were purified from putative recombinants by alkaline lysis (Maniatis et al., supra) and analyzed by electrophoresis of HindIll digests on agarose gels. The desired plasmid construct, pMYC2317, contains a toxin gene that is novel compared to the maps of other toxin genes encoding insecticidal proteins.

EXAMPLE 6

Activity of B.t. Isolates Against Mites

*B. thuringiensis* isolates of the invention were tested as spray-dried powders of fermentation broths which were concentrated by centrifugation. Pellets, which consist of water and biomass (spores, crystalline delta-endotoxins, cellular debris and growth media) were mixed with a standard carrier, preservative and surfactant. Powders, which consisted of 25% biomass, were made using a Yamato spray drier. (Sold by Yamato Scientific Co., Ltd. Tokoyo, Japan)

All broths were tested for the presence of beta-exotoxin by a larval house fly bioassay (Campbell, D. P., Dieball, D. E. and Brackett, J. M., 1987, Rapid HPLC assay for the $\beta$-exotoxin of *Bacillus thuringensis.* J. Agric. Food Chem. 35:156-158). Only isolates which tested free of $\beta$-exotoxin were used in the assays against mites.

*B. thuringiensis* isolates were tested using an artificial feeding assay. Spray-dried powders were prepared for testing by mixing 25mg of powder in 5 ml of a 10% sucrose solution. This mixture was then sonicated for 8 min to produce a suspension.

Two ml of suspension was placed in a reservoir consisting of a metal ring with a Parafilm TM film bottom. A petri dish containing approximately 30 female Two-spotted spider mites (*Tetranychus urticae*) was placed on the underside of the film. Mites were allowed to feed on the sucrose solution for 24 hrs and then transfered to 2 cm French bean leaf discs (20 mites per disc). Mortality was determined after 7 days (Table 2). Each assay was done in triplicate.

TABLE 2

Toxicity of *Bacillus thuringiensis* isolates to the two spotted spider mite, *Tetranychus urticae.* Mortality was determined after 7 days of treatment.

| Isolate | Percent Mortality |
|---|---|
| *B.t.* PS50C | 63 |
| *B.t.* PS86A1 | 85 |
| *B.t.* PS69D1 | 77 |
| *B.t.* PS72L1 | 85 |
| *B.t.* PS75J1 | 85 |
| *B.t.* PS83E5 | 70 |
| *B.t.* PS45B1 | 82 |
| *B.t.* PS24J | 90 |
| *B.t.* PS94R3 | 97 |
| *B.t.* PS17 | >90 |
| *B.t.* PS62B1 | >90 |
| *B.t.* PS74G1 | >90 |
| Control | 10 |

EXAMPLE 7

Cloning of Novel Acaride-Active Genes Using Generic Oligonucleotide Primers

The acaricidal gene of a new acaricidal B.t. isolate can be obtained from DNA of the strain by performing the standard polymerase chain reaction using the oligonucleotides of SEQ ID NO. 21 or SEQ 1D NO. 20 as reverse primers and SEQ ID NO. 10, SEQ ID NO. 11, SEQ ID NO. 16, Probe B of SEQ ID NO. 5 (AAT GAA GTAZF TAT CCA/T GTAfF AAT), or SEQ ID NO. 19 as forward primers. The expected PCR fragments would be approximately 330 to 600 bp (with either reverse primer and SEQ ID NO. 10), 1000 to 1400 bp (with either reverse primer and SEQ ID NO. 11), and 1800 to 2100 bp (with either reverse primer and any of the three N-terminal primers, SEQ ID NO. 5 (Probe B), SEQ ID NO. 16, and SEQ ID NO. 19). Alternatively, a complement from the primer family described by SEQ ID NO. 10 can be used as reverse primer with SEQ ID NO. 11, SEQ ID NO. 16, SEQ ID NO. 5 (Probe B), or SEQ ID NO. 19 as forward primers. The expected PCR fragments would be approximately 650 to 1000 bp with SEQ ID NO. 11, and 1400 to 1800 bp (for the three N-terminal primers, SEQ ID NO. 5 (Probe B), SEQ ID NO. 16, and SEQ ID NO. 19). Amplified DNA fragments of the indicated sizes can be radiolabeled and used as probes to clone the entire gene.

EXAMPLE 8

Further Cloning of Novel Acaride-Active Genes Using Generic Oligonucleotide Primers A gene coding for a acaricidal toxin of an acaricidal B.t. isolate can also be obtained from DNA of the strain by performing the standard polymerase chain reaction using oligonucleotides derived from the PS52A1 and PS69D1 gene sequences as follows:

1. Forward primer "TGATTTT(T or A)(C or A)TCAATTATAT(A or G)A(G or T)GTTYAT" (SEQ ID NO. 22) can be used with primers complementary to probe "AAGAGTTA(C or T)TA(A or G)A(G or A)AAAGTA" (SEQ ID NO. 23), probe "TTAGGACCATr(A or G)(C or T)T(T or A)GGATTTGTYGT(A or T)TATGAAAT" (SEQ ID NO. 24), and probe "GA(C or T)AGAGATGT(A or T)AAAAT(C or T)(T or A)TAGGAATG" (SEQ ID NO. 25) to produce amplified fragments of approximately 440, 540, and 650 bp, respectively.

2. Forward primer "TT(A or C)TTAAA(A or T)C(A or T)GCTAATGATATT" (SEQ ID NO. 26) can be used with primers complementary to SEQ ID NO. 23, SEQ ID NO. 24, and SEQ ID NO. 25 to produce amplified fragments of approximately 360, 460, and 570 bp, respectively.

3. Forward primer SEQ ID NO. 23 can be used with primers complementary to SEQ ID NO. 24 and SEQ ID NO. 25 to produce amplified fragments of approximately 100 and 215 bp, respectively.

Amplified DNA fragments of the indicated sizes can be radiolabeled and used as probes to clone the entire gene.

EXAMPLE 9

Insertion of Toxin Genes Into Plants

One aspect of the subject invention is the transformation of plants with genes coding for a acaricidal toxin. The transformed plants are resistant to attack by acarides.

Genes coding for acaricidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence coding for the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: The Binary Plant Vector System, Offset-durkkerij Kanters B.V., Alblasserdam, Chapter 5; Fraley et al., Crit. Rev. Plant Sci. 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into Agrobacterium tumefaciens by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] Mol. Gen. Genet. 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 10

Cloning of *Bacillus thuringiensis* Genes Into Baculoviruses

The genes coding for the insecticidal toxins, as disclosed herein, can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Penhock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The genes coding for the protein toxins of the invention can be modified with BamHI linkers at appropriate regions both upstream and downstream from the coding region and inserted into the passenger site of one of the AcNPV vectors.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated DNA encoding a δ-endotoxin which is active against acarides wherein said gene is obtained from a *Bacillus thuringiensis* isolate selected from the group consisting of B.t. PS72L1, B.t. PS75J1, B.t. PS83E5, B.t. PS45B1, B.t. PS24J, B.t. PS94R3, B.t. PS62B1 and B.t. PS74G1.

2. A transformed host selected from the group consisting of a microbe and a baculovirus transformed by a gene encoding a δ-endotoxin active against acarides, wherein said gene is obtained from a *Bacillus thuringiensis* isolate selected from the group consisting of B.t. PS72L1, B.t. PS75J1, B.t. PS83E5, B.t. PS45B1, B.t. PS24J, B.t. PS94R3, B.t. PS62B1 and B.t. PS74G1.

* * * * *

UNITED STATES PATENT AND TRADEMARK OFFICE

CERTIFICATE OF CORRECTION

PATENT NO. : 5,424,410

DATED : June 13, 1995

INVENTOR(S) : Jewel M. Payne, et al

It is certified that error appears in the above-indentified patent and that said Letters Patent is hereby corrected as shown below:

Column 1, line 49: Delete "HaH, F.R." and insert --Hall, F.R.--.

Column 3, lines 34: Delete "PS50C." and insert --PS86A1.--

Column 3, line 36: Delete "PS50C." and insert --PS86A1.--

Column 3, line 38: Delete "PS86A1." and insert --PS50C.--

Column 3, line 40: Delete "PS86A1." and insert --PS50C.--

Column 3, line 64: Delete "equivalent toms)" and insert --equivalent toxins)--.

Column 5, line 3: Delete "amorphie," and insert --amorphic,--.

Column 6, line 10: Delete "$^{32}$p, $^{125}$i," and insert --$^{32}$P, $^{125}$I,--.

Column 7, line 6: Delete "hornology" and insert --homology--.

Column 8, line 22: Delete "(pNffC 2321)" and insert --(pMYC 2321)--.

Column 8, line 23: Delete "(pNffc 1627)" and insert --(pMYC 1627)--.

UNITED STATES PATENT AND TRADEMARK OFFICE

CERTIFICATE OF CORRECTION

PATENT NO. : 5,424,410

DATED : June 13, 1995

INVENTOR(S) : Jewel M. Payne, et al

It is certified that error appears in the above-indentified patent and that said Letters Patent is hereby corrected as shown below:

Column 8, line 63: Delete "ataritidal - effective" and insert --acaricidal - effective--.

Column 9, line 6: Delete "thuringiens" and insert --thuringiensis--.

Column 9, line 34: Delete "102 to" and insert --$10^2$ to--.

Column 10, line 21-22: Delete "Eustimanatophyceae," and insert --Eustigmatophyceae,--

Column 10, line 34: Delete "Kluyverornyces" and insert --Kluyveromyces--.

Column 10, line 63: Delete "to xin," and insert --toxin,--.

Column 14, line 6: Delete "the B.t , spores" and insert --the B.t. spores--.

Column 14, line 39: Delete "routants" and insert --mutants--.

Column 15, line 28: Delete "$CaC1_2$ Solution (100 ml) 3.66 g
$CaC1_22H_2O$"

and insert --$CaC1_2$ Solution (100 ml)
$CaC1_2 \cdot 2H_2O$ 3.66 g--

UNITED STATES PATENT AND TRADEMARK OFFICE

CERTIFICATE OF CORRECTION

PATENT NO. : 5,424,410 Page 3 of 5

DATED : June 13, 1995

INVENTOR(S) : Jewel M. Payne, et al

It is certified that error appears in the above-indentified patent and that said Letters Patent is hereby corrected as shown below:

Column 16, line 27: Delete "[$^{32}$p]" and insert --[$^{32}$P]--.

Column 16, line 30: Delete "(GCAATITFAAATGAATrATATCC)" and insert --(GCAATTTTAAATGAATTATATCC)--.

Column 16, line 46: Delete "KW25 1 E. coli" and insert --KW251 E. coli--.

Column 17, line 6: Delete "S-Bromo" and insert --5-Bromo--.

Column 17, line 9: Delete "(Beta)galactosidase" and insert --(Beta) - galactosidase--.

Column 18, line 12: Delete "BarnHI" and insert --BamHI--.

Column 18, line 21: Delete "SaII" and insert --SalI--.

Column 18, line 38: Delete "putalive" and insert --putative--.

Column 18, line 38: Delete "(ManiaIls" and insert --(Maniatis--.

Column 18, line 46: Delete "electropotation" and insert --electroporation--.

Column 18, line 58: Delete "69D1D" and insert --69D1-D--.

UNITED STATES PATENT AND TRADEMARK OFFICE

CERTIFICATE OF CORRECTION

PATENT NO. : 5,424,410

DATED : June 13, 1995

INVENTOR(S) : Jewel M. Payne, et al

It is certified that error appears in the above-indentified patent and that said Letters Patent is hereby corrected as shown below:

Column 19, line 22: Delete "HindlII" and insert --HindIII--.

Column 19, line 28: Delete "HindlII - digested pHTBluell" and insert --HindIII - digested pHTBlueII--.

Column 19, line 39: Delete "Hindlll" and insert --HindIII--.

Column 20, line 43: Delete "SEQ lD NO." and insert --SEQ ID NO.--.

Column 20, lines 45-46: Delete "(AAT GAA GTAZF TAT CCA/T GTAfF AAT)" and insert --(AAT GAA GTA/T TAT CCA/T GTA/T AAT)--.

Column 21, line 12: Delete "GTTYAT" and insert --GTTTAT--.

Column 21, line 16: Delete "CATr(A" and insert --CATT(A--.

Column 21, lines 16-17: Delete "GGATTTGTYGT" and insert --GGATTTGTTGT--.

Column 24, line 4: Delete "Penhock et al." and insert --Pennock et al.--.

UNITED STATES PATENT AND TRADEMARK OFFICE

CERTIFICATE OF CORRECTION

PATENT NO. : 5,424,410

DATED : June 13, 1995

INVENTOR(S) : Jewel M. Payne, et al

It is certified that error appears in the above-indentified patent and that said Letters Patent is hereby corrected as shown below:

Column 77, line 48: Delete "said gene is" and insert --said DNA is--.

Column 78, line 47: Delete "gene encoding" and insert --DNA encoding--.

Column 78, line 48: Delete "said gene is" and insert --said DNA is--.

Signed and Sealed this

Nineteenth Day of September, 1995

Attest:

BRUCE LEHMAN

*Attesting Officer*

*Commissioner of Patents and Trademarks*